United States Patent
D'Oosterlynck et al.

(10) Patent No.: US 7,387,999 B2
(45) Date of Patent: Jun. 17, 2008

(54) SIMMONDSIN FOR USE AS ANGIOGENESIS INHIBITOR

(75) Inventors: André D'Oosterlynck, Museumlaan 17, B-9830, Sint-Martens-Latem (BE); Stefaan Raes, Merelbeke (BE)

(73) Assignee: André D'Oosterlynck, Sint-Martens-Latem (BE)

( * ) Notice: Subject to any disclaimer, the term of this patent is extended or adjusted under 35 U.S.C. 154(b) by 368 days.

(21) Appl. No.: 10/520,580

(22) PCT Filed: Jul. 7, 2003

(86) PCT No.: PCT/EP03/07270

§ 371 (c)(1),
(2), (4) Date: Apr. 26, 2005

(87) PCT Pub. No.: WO2004/004746

PCT Pub. Date: Jan. 15, 2004

(65) Prior Publication Data

US 2006/0088613 A1    Apr. 27, 2006

(30) Foreign Application Priority Data

Jul. 8, 2002    (BE) ................... 2002/0428

(51) Int. Cl.
*A61K 31/70*    (2006.01)
(52) U.S. Cl. ...................................... 514/25
(58) Field of Classification Search .................... None
See application file for complete search history.

(56) References Cited

U.S. PATENT DOCUMENTS 5,672,371 A * 9/1997 d'Oosterlynck ............. 426/430

FOREIGN PATENT DOCUMENTS

EP    1616874 A1 *  1/2006

WO    WO94/25035 A1 * 11/1994

OTHER PUBLICATIONS (R) Flo et al., "Effect of Simmondsin Derivatives on Food Intake: Dose-Response Curves in Rats," Journal of Agriculture and Food Chemistry, 46(5), 1910-1913 (1998); Web published on Apr. 11, 1998.*
(R) Flo et al., "Effect of Simmondsin Derivatives on Food Intake: Dose-Response Curves in Rats," □□Journal of Agriculture and Food Chemistry, 46(5), 1910-1913 (1998); Web published on Apr. 11, 1998.*

* cited by examiner

*Primary Examiner*—S. Anna Jiang
*Assistant Examiner*—L. E. Crane
(74) *Attorney, Agent, or Firm*—Knobbe, Martens, Olson & Bear, LLP

(57)    ABSTRACT

Methods of inhibiting angiogenesis in humans and animals by administering a effective amount of a secondary plant metabolite from jojoba, having the general formula I shown below, are disclosed. Preferred compounds having general formula I include 4-desmethylsimmondsin, 5-desmethyl-simmondsin, 4,5-didesmethylsimmondsin, 4,5-dimethyl-simmondsin, 4-desmethylsimmondsin-2'-ferulate, 5-desmethylsimmondsin-2'-ferulate, 4,5-didesmethylsimmondsin-2'-ferulate and 4,5-dimethylsimmondsin-2'-ferulate. Such compounds can be synthesized chemically according to well known techniques or can be isolated from refined and de-oiled jojoba flour by conventional extraction techniques using polar solvents such as a ketone or a low boiling point alcohol. Pharmaceutical compositions for inhibiting angiogenesis or for treating angiogenesis-related diseases in humans or animals are disclosed General Formula 1

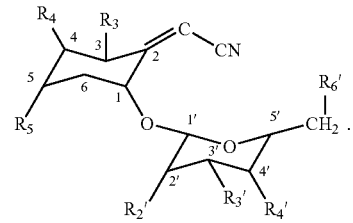

12 Claims, 16 Drawing Sheets

SIMMONDSIN FOR USE AS ANGIOGENESIS INHIBITOR

CROSS-REFERENCE TO RELATED APPLICATIONS

This application is the U.S. National Phase under 35 U.S.C. § 371 of International Application PCT/EP2003/007270, filed Jul. 7, 2003, which claims priority of BE 2002/0428, filed Jul. 8, 2002.

FIELD OF THE INVENTION

The invention essentially relates to new uses of active components derived from the jojoba plant (*Simmondsia chinensis* L., C. K. Schneider). In particular, the invention relates to the use of active components derived from jojoba as a medicament and for the manufacture of a medicament for inhibiting angiogenesis or for treating angiogenesis-related diseases.

BACKGROUND

*Simmondsia chinensis*, commonly referred to as jojoba, is a native oilseed shrub of the Sonoran desert, including parts of Arizona, California and Mexico. The principal product extracted from the seeds is a liquid wax with characteristics similar to sperm whale oil. Jojoba oil is frequently applied as an additive in mineral oils and cosmetics.

Jojoba seed meal or flour is a by-product of the oil extraction of the seeds of the jojoba plant. Preparation of refined, de-oiled jojoba flour has been described previously, particularly in international patent application WO 94/25035. A polar extract of this refined, de-oiled jojoba flour is constituted mainly of simmondsin and its derivatives.

Defatted (de-oiled) jojoba seed meal contains approximately 30% proteins, and its supplementation in animal feed has been reported as associated with food intake reduction and growth retardation (Booth et al. 1974; Life Sci. 15:1115-1120; Verbiscar et al. 1980; Agric. Food Chem. 28:571-578). Later studies described food intake control properties after oral administration of 4,5-dimethylsimmondsin and its ferulate present in jojoba flour (Flo et al., 1998; J. Agric. Food Chem. 46:1910-1913).

It is an object of the present invention to provide novel uses of active components derived from the jojoba plant. It is another object of the invention to provide novel uses of simmondsins.

SUMMARY OF THE INVENTION

The invention is based on the unexpected finding that active substances isolated from the jojoba plant, and in particular simmondsins, esters or salts thereof, have a potent angiogenesis-inhibiting effect.

Angiogenesis or neovascularisation, are used herein as synonyms and relate to the phenomenon of the formation of new blood vessels. Angiogenesis is important in many pathologies in all parts of the body, involving all disciplines of medicine. The present invention therefore, relates in a first aspect to the use of an active component derived from jojoba for the manufacture of a medicament for inhibiting angiogenesis. In particular, the invention relates to the use of a simmondsin, stereoisomeric forms, racemic mixtures, metabolites, esters or salts thereof, or mixtures thereof for the manufacture of a medicament for inhibiting angiogenesis. The present invention also relates to the use of an active component derived from jojoba or of a simmondsin, stereoisomeric forms, racemic mixtures, metabolites, esters or salts thereof, or mixtures thereof, for the manufacture of a medicament for treating angiogenesis-related diseases.

In another aspect, the invention provides a pharmaceutical composition comprising a therapeutically effective amount of an active component derived from jojoba, and in particular comprising a therapeutically effective amount of a simmondsin, stereoisomeric forms, racemic mixtures, metabolites, esters or salts thereof, or mixtures thereof, and a pharmaceutical acceptable excipient for inhibiting angiogenesis or for treating angiogenesis-related diseases in humans or animals.

The present invention further relates to a method of inhibiting angiogenesis and to a method of treating angiogenesis-related diseases in humans and animals comprising administering to the human or animal in need thereof a therapeutically effective amount of an active component derived from jojoba, and in particular a therapeutically effective amount of a simmondsin, stereoisomeric forms, racemic mixtures, metabolites, esters or salts thereof, or mixtures thereof.

It results from the above and from the following description that the present invention provides an unexpected and unambiguously technical advance by inhibiting angiogenesis or by permitting the treatment of angiogenesis-related diseases by potent angiogenesis-inhibiting properties of active components derived from jojoba.

Other objects and advantages of the present invention will become apparent from the following detailed description taken in conjunction with the accompanying figures and examples.

DETAILED DESCRIPTION OF THE FIGURES

DETAILED DESCRIPTION OF THE INVENTION

Figure 1:
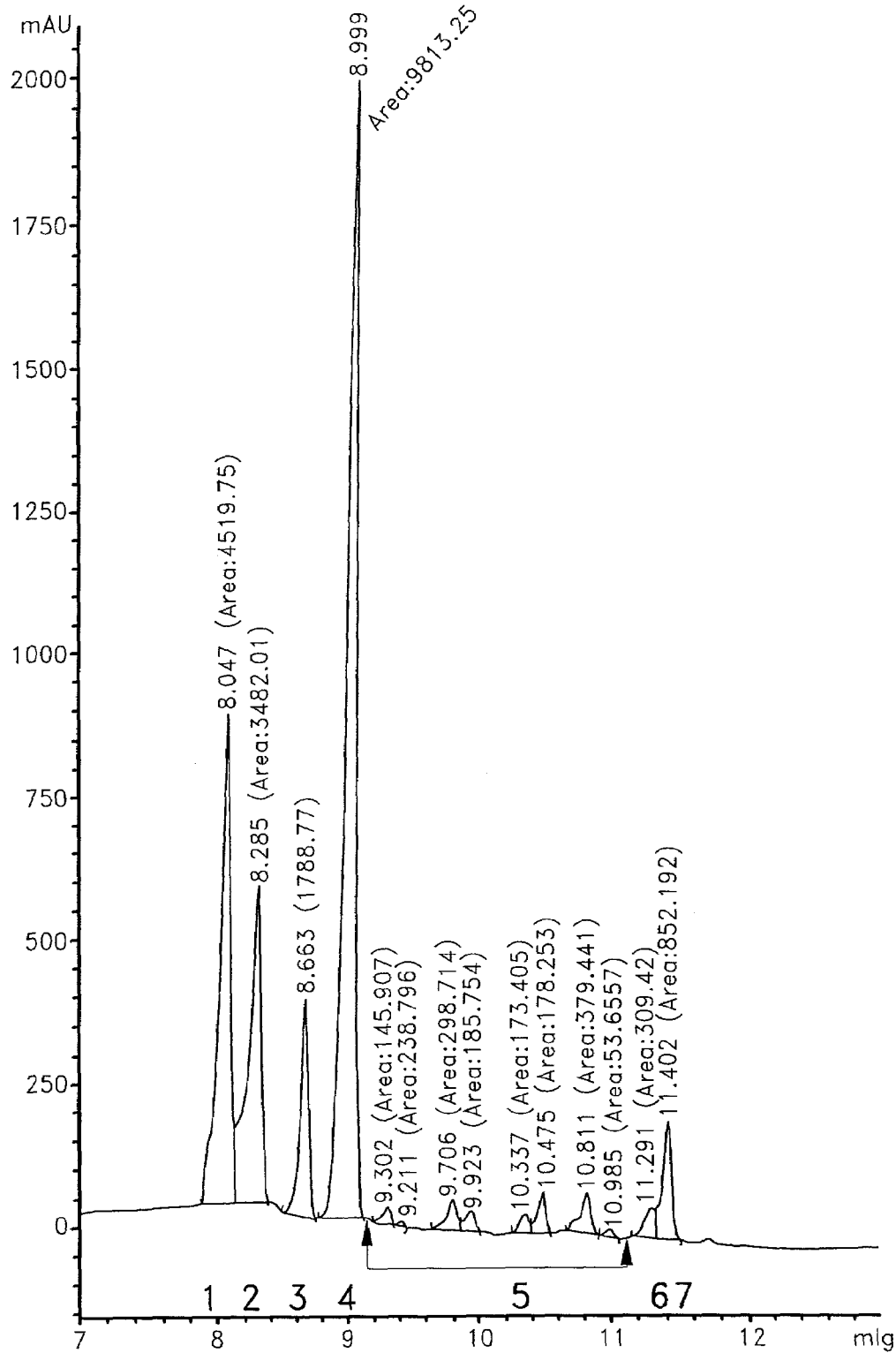
FIG. 1 represents a HPLC chromatogram of a total polar extract from refined, de-oiled jojoba flour.

The present invention relates to novel uses and applications of active components derived from jojoba and in particular to novel uses and applications of simmondsins.

As used herein the term "jojoba", "jojoba plant" or a similar term refers to the plant belonging to the *Simmondsia* spp. A particular example of such plant is known under the name of *Simmondsia chinensis* L., C. K. Schneider.

Whenever used in the present invention the term "active components" or a similar term is meant to include components that are derived or isolated from the jojoba plant. It is to be understood that these active components can be derived or isolated from all parts of the jojoba plant, including leafs, seeds, roots, branches, shoots, etc. . . . The term active components as used herein is also meant to include apart from other parts of the jojoba plant mentioned above, jojoba flour, or an extract from jojoba flour. The term also includes compounds that are contained in jojoba flour or in jojoba extract, such as simmondsins having the general formula (I) as defined below.

The term "jojoba flour" as used herein refers to flour, which is obtained from the jojoba plant, and in particular, which is obtained from the jojoba seeds. This term refers to non-treated or treated, for instance de-oiled, heated etc. forms of the flour. Preferably, the term jojoba flour refers to refined and de-oiled jojoba seed meal.

Jojoba meal is readily available, with it being a by-product of oil extraction process of the seeds of the jojoba plant. Jojoba flour can be prepared according to methods known in the art. Jojoba flour is generally considered as being a waste product in the preparation process of jojoba oil, and is discarded, which is economically relatively cost effective. Surprisingly, the present invention now provides an economically valuable use for the jojoba flour, in particular as a medicine, more in particular a medicine for inhibiting angiogenesis, and as a source for extracting valuable compounds comprised in the flour, which have medicinal activity.

The term "jojoba extract" or "extract" or similar terms as used herein refer to an extract, which is obtained from the jojoba flour using a polar solvent, such as for instance a mixture of aceton/water (95/5).

The jojoba extract according to the invention may be obtained from jojoba seeds according to techniques known in the art. For instance, jojoba seeds are first treated as to separate seed meal from the seed peal. Then the jojoba flour, which contains approximately 60% oil and 40% dry matter, is extracted with a solvent, e.g. an aceton/hexane (1/9) solvent. The oil fraction is removed and the dry matter (i.e. the meal), which contains approximately 50% sugars, 30% proteins, 10% water and between 5 and 10% of simmondsin, is further treated. The dry matter (meal) is then extracted, e.g. with an aceton/water (95/5) solvent to result in a polar extract.

It shall be clear from the description, further provided below, that this polar extract according to the invention comprises compounds that are naturally occurring in jojoba, and in particular comprises the compounds 4-desmethylsimmondsin, 5-desmethylsimmondsin, 4,5-didesmethylsimmondsin, 4,5-dimethylsimmondsin, 4-desmethylsimmondsin-2'-ferulate, 5-desmethylsimmondsin-2'-ferulate, 4,5-didesmethylsimmondsin-2'-ferulate and 4,5-dimethylsimmondsin-2'-ferulate.

The term "simmondsin" or "simmondsins" as used in the present application refers to substantially pure forms of simmondsin as well as to simmondsin derivatives, i.e. all sources and administrable forms of substances derived from or related to simmondsin, or any mixtures thereof. The term simmondsin as used in the present application is meant to encompass all compounds having general formula (I), and stereoisomeric forms, racemic mixtures, metabolites, similar compounds made by synthesis, (pharmaceutically acceptable) esters, salts or mixtures thereof,

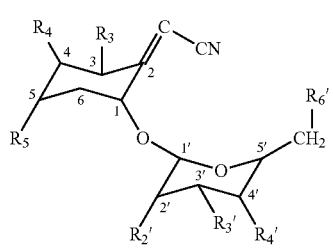

Formula (I)

wherein $R_4$ and $R_5$ are independently selected from the group comprising oxo, hydrogen, hydroxyl, alkyl, alkenyl, alkynyl, alkyloxy, alkyloxyalkyl, alkylthioalkyl, alkyloxycarbonyl, alkylthiocarbonyl, alkanoyl, cycloalkyl, cycloalkylalkyl, cycloalkylcarbonyl, cycloalkylalkanoyl, cycloalkylthiocarbonyl, cycloalkylalkoxycarbonyl, cycloalkylalkoxythiocarbonyl, cycloalkylthioalkyl, alkylcarbonyloxyalkyl, arylcarbonyloxyalkyl, cycloalkylcarbonyloxyalkyl, silyloxyalkyl, aryl, aralkyl, arylalkenyl, arylcarbonyl, aryloxycarbonyl, arylthiocarbonyl, aralkoxycarbonyl, arylalkylthiocarbonyl, aryloxyalkyl, arylthioalkyl, haloalkyl, hydroxyalkyl, aralkanoyl, aroyl, aryloxycarbonylalkyl, aryloxyalkanoyl, carboxyl, formyl, alkenylcarbonyl, alkynylcarbonyl, cyano, aminocarbonyl, aminoalkanoyl, aminoalkyl, $CR^6=NR^7$ or $CR^6=N(OR^7)$, with $R^6$ and $R^7$ being independently selected from the group comprising hydrogen, hydroxyl, alkyl, aryl, alkenyl, alkynyl, aminoalkyl, aminoaryl, alkylcarbonylamino, arylcarbonylamino alkylthiocarbonylamino and arylthiocarbonylamino; and wherein $R_3$, $R_2'$, $R_3'$ $R_4'$, and $R_6'$ are independently selected from the group comprising hydroxyl or an ester.

Whenever used hereinafter, the term "compounds according to the invention", or "the present compounds" or a similar term is meant to include compounds having general formula (I) as defined above and stereoisomeric forms, racemic mixtures, metabolites, esters or salts thereof, or any mixture thereof.

The compounds according to the invention can be isolated or derived from the jojoba plant. It shall be understood that this term also encompasses compounds according to the invention that are not derived from the jojoba plant but that are chemically synthesised according to techniques that are known in the art.

In a preferred embodiment the invention relates to a simmondsin, as defined above, which naturally occurs in jojoba and which is comprised within jojoba flour or a jojoba extract. In another preferred embodiment the invention relates to a simmondsin, as defined above which is synthetically prepared.

The term "stereoisomeric forms" of compounds of the present invention, as used herein, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers forms of the basic molecular structure of said compound. All stereochemically isomeric forms of the compounds of the present invention both in substantially pure form or in admixture with each other are intended to be embraced within the scope of the present invention.

The term "diastereomers" refers to stereoisomers that are not enantiomers; i.e. that have different chemical and physical properties. The term "enantiomers" refers to compounds which are non-superimposable, i.e. which have different mirror images; but having a vast majority of chemical and physical properties being identical. The term "racemic mixture" refers to mixtures of enantiomers, diastereomers or combinations thereof.

Pure stereoisomeric forms of the compounds as mentioned herein are defined as isomers substantially free of other enantiomeric or diastereomeric forms of the same basic molecular structure of said compounds. In particular, the term 'stereoisomerically pure' concerns compounds having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds of this invention may be obtained by the application of art-known procedures. For instance, enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods which may advantageously be employed are, for example, selective crystallization and chromatography, e.g. column chromatography.

The term "metabolite" according to the present invention refers to a product or a simmondsin compound which is the result of metabolism, i.e. the result of physical an/or chemical processes by which the product is produced, maintained or destroyed.

The term "esters" according to the invention includes the conventional non-toxic esters which are formed, e.g., from inorganic or organic acids. Examples of such acid addition esters include but are not limited to acetate, adipate, alginate, aspartate, benzoate, benzenesulfonate, bisulfate, butyrate, citrate, camphorate, camphorsulfonate, cyclopentanepropionate, digluconate, dodecylsulfate, erucate, ethanesulfonate, ferulate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, undecanoate and valerate.

The type of esterification can greatly determine the biological activity of the simmondsin compound according to the present invention.

The term esters as used in the present invention is meant to include esters, as defined above, that can be isolated or derived from the jojoba plant. It shall be understood that this term also includes esters that can be chemically synthesised according to techniques that are known in the art. Examples of esters according to the invention comprise but are not limited to simmondsin ferulate, dimethylsimmondsin ferulate, desmethylsimmondsin ferulate and didesmethylsimmondsin ferulate.

For therapeutic use, the "salts" of the compounds of formula (I) are those wherein the counterion is pharmaceutically or physiologically acceptable. However, salts having a pharmaceutically unacceptable counterion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids.

Conversely said acid addition salt forms can be converted by treatment with an appropriate base into the free base form.

The compounds of formula (I) containing an acidic proton may also be converted into their non-toxic metal or amine addition salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms which the compounds of the present invention are able to form. Examples of such forms are e.g. hydrates, alcoholates and the like.

The term "substantially pure" as used herein refers to a purity of more than 80% and preferably more than 90% and more preferred more than 99%.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

As used herein, the term "halo" or "halogen" as a group or part of a group is generic for fluoro, chloro, bromo or iodo.

The term "alkyl", alone or in combination, means straight and branched chained saturated hydrocarbon radicals containing from 1 to 10 carbon atoms, preferably from 1 to 8 carbon atoms, more preferably 1 to 6 carbon atoms. Examples of such radicals include methyl, ethyl, n-propyl, isopropyl, n-butyl, isobutyl, sec-butyl, tert-butyl, 2-methylbutyl, pentyl, iso-amyl, hexyl, 3-methylpentyl, octyl and the like.

The term "alkenyl", alone or in combination, defines straight and branched chained hydrocarbon radicals containing from 2 to about 30 carbon atoms, preferably 2 to 18 carbon atoms, preferably from 2 to 8 carbon atoms, more preferably 2 to 6 carbon atoms containing at least one double bond such as, for example, ethenyl, propenyl, butenyl, pentenyl, hexenyl and the like.

The term "alkynyl", alone or in combination, defines straight and branched chained hydrocarbon radicals having from 2 to 10 carbon atoms containing at least one triple bond, more preferably from 2 to about 6 carbon atoms. Examples of alkynyl radicals include ethynyl, propynyl, (propargyl), butynyl, pentynyl, hexynyl and the like.

The term "cycloalkyl" alone or in combination, means a saturated or partially saturated monocyclic, bicyclic or polycyclic alkyl radical wherein each cyclic moiety contains from about 3 to about 8 carbon atoms, more preferably from about 3 to about 7 carbon atoms. Examples of monocyclic cycloalkyl radicals include cyclopropyl, cyclobutyl, cyclopentyl, cyclohexyl, cycloheptyl, cyclooctyl and the like. Examples of polycyclic cycloalkyl radicals include decahydronaphthyl, bicyclo [5.4.0] undecyl, adamantyl, and the like.

The term "cycloalkylalkyl" means an alkyl radical as defined herein, in which at least one hydrogen atom on the alkyl radical is replaced by a cycloalkyl radical as defined herein. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, 3-cyclopentylbutyl, cyclohexylbutyl and the like.

The term "aryl" alone or in combination, is meant to include phenyl and naphtyl which both may be optionally substituted with one or more substituents independently selected from alkyl, alkoxy, halogen, hydroxy, amino, nitro, cyano, haloalkyl, carboxy, alkoxycarbonyl, cycloalkyl, Het$^1$, amido, optionally mono- or disubstituted aminocarbonyl, methylthio, methylsulfonyl, and phenyl optionally substituted with one or more substituents selected from $C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, Het$^1$, optionally mono- or disubstituted aminocarbonyl, methylthio and methylsulfonyl; whereby the optional substituents on any amino function are independently selected from alkyl, alkyloxy, Het$^1$, Het$^1$alkyl, Het$^1$alkyl, Het$^1$oxy, Het$^1$oxyalkyl, phenyl, phenyloxy, phenyloxyalkyl, phenylalkyl, alkyloxycarbonylamino, amino, and aminoalkyl whereby each of the amino groups may optionally be mono- or where possible disubstituted with alkyl. Examples of aryl includes phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphtyl, 2-naphthyl, 3-amino-1-naphthyl, 2-methyl-3-amino-1-naphthyl, 6-amino-2-naphthyl, 4,6-dimethoxy-2-naphthyl and the like.

The term "aralkyl" alone or in combination, means an alkyl as defined herein, wherein an alkyl hydrogen atom is replaced by an aryl as defined herein. Examples of aralkyl radicals include benzyl, phenethyl, dibenzylmethyl, methylphenylmethyl, 3-(2-naphthyl)-butyl, and the like.

As used herein, the term "oxo" or "=O" forms a carbonyl moiety with the carbon atom to which it is attached.

The term "formyl" or "—CHO" is an aldehyde moiety whereby the C atom binds to the carbon atom to which it is attached.

As used herein, the term "carboxyl" or "—COOH" is an acid moiety whereby the carbon atom binds to the carbon atom to which it is attached.

The term "haloalkyl" alone or in combination, means an alkyl radical having the meaning as defined above wherein one or more hydrogens are replaced with a halogen, preferably, chloro or fluoro atoms, more preferably fluoro atoms. Examples of such haloalkyl radicals include chloromethyl, 1-bromoethyl, fluoromethyl, difluoromethyl, trifluoromethyl, 1,1,1-trifluoroethyl and the like.

The term "alkoxy" or "alkyloxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy, hexanoxy and the like.

The term "alkanoyl" or "alkylcarbonyl", alone or in combination, means an acyl radical derived from an alkanecarboxylic acid, examples of which include acetyl, propionyl, butyryl, valeryl, 4-methylvaleryl, and the like.

The term "alkylamino" means an alkyl amine radical, wherein the term "alkyl" is defined as above. Examples of alkylamino radicals include methylamino ($NHCH_3$), ethylamino ($NHCH_2CH_3$), n-propylamino, isopropylamino, n-butylamino, isobutylamino, sec-butylamino, tert-butylamino, n-hexylamino, and the like.

The term "alkylthio" means an alkyl thioether radical, wherein the term "alkyl" is defined as above. Examples of alkylthio radicals include methylthio ($SCH_3$), ethylthio ($SCH_2CH_3$), n-propylthio, isopropylthio, n-butylthio, isobutylthio, sec-butylthio, tert-butylthio, n-hexylthio, and the like.

The term "aminoalkanoyl" means an acyl group derived from an amino-substituted alkylcarboxylic acid wherein the amino group can be a primary, secondary or tertiary amino group containing substituents selected from alkyl, aryl, aralkyl, cycloalkyl, cycloalkylalkyl radicals and the like.

The term "aminocarbonyl" alone or in combination, means an amino-substituted carbonyl (carbamoyl) group wherein the amino group can be a primary, secondary or tertiary amino group containing substituents selected from alkyl, aryl, aralkyl, cycloalkyl, cycloalkylalkyl radicals and the like.

The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like.

The term "aralkoxy" means alkoxy as defined herein, wherein an alkyl hydrogen atom is replaced by an aryl as defined herein. Examples of aralkoxy radicals include 2-phenylethoxy, 2-phenyl-1-propoxy, and the like.

The term "aralkoxycarbonyl", alone or in combination, means a radical of the formula aralkyl-O—C(O)— in which the term "aralkyl" has the significance given above. Examples of an aralkoxycarbonyl radical are benzyloxycarbonyl and 4-methoxyphenylmethoxycarbonyl.

The term "aroyl" means an acyl radical derived from an arylcarboxylic acid, aryl having the meaning given above. Examples of such arylcarboxylic acid radicals include substituted and unsubstituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamidol)-2-naphthoyl, and the like.

The term "arylaminoalkyl" means alkyl as defined herein, wherein an alkyl hydrogen atom is replaced by an arylamino as defined herein. Examples of arylaminoalkyl radicals include phenylaminoethyl, 4-(3-methoxyphenylamino)-1-butyl, and the like.

The term "aryloxyalkoxy" means alkoxy as defined herein, wherein an alkyl hydrogen atom is replaced by an aryloxy as defined herein. Examples of (aryloxy) alkoxy radicals include 2-phenoxyethoxy, 4-(3-aminophenoxy)-1-butoxy, and the like.

The term "cycloalkylalkoxycarbonyl" means an acyl group derived from a cycloalkylalkoxycarboxylic acid of the formula cycloalkylalkyl-O—COOH wherein cycloalkylalkyl has the meaning given above.

The term "cycloalkylcarbonyl" means an acyl group derived from a monocyclic or bridged cycloalkanecarboxylic acid such as cyclopropylcarbonyl, cyclohexylcarbonyl, adamantylcarbonyl, and the like, or from a benzo-fused monocyclic cycloalkanecarboxylic acid which is optionally substituted by one or more substituents selected from alkyl, alkoxy, halogen, hydroxy, amino, nitro, cyano, haloalkyl, carboxy, alkoxycarbonyl, cycloalkyl, heterocycloalkyl, alkanoylamino, amido, mono and dialkyl substituted amino, mono and dialkyl substituted amido and the like, such as 1,2,3,4-tetrahydro-2-naphthoyl, 2-acetamido-1,2,3,4-tetrahydro-2-naphthoyl.

As used herein before, the term "one or more" covers the possibility of all the available C-atoms, where appropriate, to be substituted, preferably, one, two or three. When any variable, e.g. halogen or alkyl, occurs more than one time in any constituent, each definition is independent.

A particular group of compounds are those compounds of formula (I) wherein $R_4$ and $R_5$ are independently selected from the group comprising oxo, hydrogen, hydroxyl, alkyl, alkenyl, alkynyl, alkyloxy, alkyloxyalkyl, alkylthioalkyl, alkyloxycarbonyl, alkylthiocarbonyl, alkanoyl, alkylcarbonyloxyalkyl, arylcarbonyloxyalkyl, silyloxyalkyl, haloalkyl, hydroxyalkyl, carboxyl, formyl, alkenylcarbonyl, alkynylcarbonyl, cyano, aminocarbonyl, aminoalkanoyl, aminoalkyl, and wherein $R_3$, $R_2'$, $R_3'$ $R_4'$, and $R_6'$ are independently selected from the group comprising hydroxyl or an ester as defined above.

Another particular group of compounds are those compounds of formula (I) wherein $R_4$ and $R_5$ are independently selected from the group comprising oxo, hydrogen, hydroxyl, alkyl, alkyloxy, alkyloxyalkyl, carboxyl, and wherein $R_3$, $R_2'$, $R_3'$ $R_4'$, and $R_6'$ are independently selected from the group comprising hydroxyl or an ester as defined above.

In a preferred embodiment, the compounds according to the invention are compounds represented by formula (I), and stereoisomeric forms, racemic mixtures, metabolites, esters, or salts thereof, wherein $R_4$ and $R_5$ are independently selected from the group comprising hydroxyl, alkyl or alkyloxy, and wherein $R_3$, $R_2'$, $R_3'$ $R_4'$, and $R_6'$ are independently selected from the group comprising hydroxyl or an ester as defined above.

In a more preferred embodiment, the compounds according to the invention are compounds represented by formula (I), and stereoisomeric forms, racemic mixtures, metabolites, esters, or salts thereof, wherein $R_4$ and $R_5$ are independently selected from the group comprising —OH or —OCH$_3$, and wherein $R_3$, $R_2'$, $R_3'$ $R_4'$, and $R_6'$ are independently selected from the group comprising hydroxyl or an ester as defined above.

In a preferred embodiment, said ester is erucate, ferulate, valerate or acetate, and preferably ferulate. Ferulic acid occurs in 2 (cis/trans) isomers. Therefore, in another preferred embodiment said ferulate is a cis or a trans ferulate.

In another preferred embodiment, the compounds according to the invention are compounds represented by formula (I), and stereoisomeric forms, racemic mixtures, metabolites, esters, or salts thereof, wherein $R_4$ and $R_5$ are —OH and wherein $R_3$, $R_2'$, $R_3'$ $R_4'$, and $R_6'$ are independently selected from the group comprising hydroxyl or an ester as defined above.

In a particularly preferred embodiment, the compounds according to the invention is represented by formula (I) wherein $R_4$ and $R_5$ are —OH and $R_3$. $R_2'$, $R_3'$ $R_4'$, and $R_6'$ are —OH. Said compound is referred to as 4,5-didesmethylsimmondsin.

In another particularly preferred embodiment, the compounds according to the invention is represented by formula (I) wherein $R_4$ and $R_5$ are —OH, wherein $R_3$, $R_3'$ $R_4'$, and $R_6'$ are —OH, and wherein $R_2'$ is ferulate. Said compound is referred to as 4,5-didesmethylsimmondsin-2'-ferulate.

In another preferred embodiment, the compounds according to the invention are represented by formula (I) wherein $R_4$ is —OCH$_3$ and $R_5$ is —OH and wherein $R_3$, $R_2'$, $R_3'$ $R_4'$, and $R_6'$ are independently selected from the group comprising hydroxyl or an ester as defined above.

In a particularly preferred embodiment, the compound according to the invention is represented by formula (I) wherein $R_4$ is —OCH$_3$ and $R_5$ is —OH and wherein $R_3$, $R_2'$, $R_3'$ $R_4'$, and $R_6'$ are —OH. Said compound is referred to as 5-desmethylsimmondsin.

In another particularly preferred embodiment, the compounds according to the invention is represented by formula (I) wherein $R_4$ is —OCH$_3$ and $R_5$ is —OH, wherein $R_3$, $R_3'$ $R_4'$, and $R_6'$ are —OH, and wherein $R_2'$ is ferulate. Said compound is referred to as 5-desmethylsimmondsin-2'-ferulate.

In another preferred embodiment, the compounds according to the invention are represented by formula (I) wherein $R_4$ is —OH and $R_5$ is —OCH$_3$ and wherein $R_3$, $R_2'$, $R_3'$ $R_4'$, and $R_6'$ are independently selected from the group comprising hydroxyl or an ester as defined above.

In a particularly preferred embodiment, the compound according to the invention is represented by formula (I) wherein $R_4$ is —OH and $R_5$ is —OCH$_3$, and wherein $R_3$, $R_2'$, $R_3'$ $R_4'$, and $R_6'$ are —OH. Said compound is referred to as 4-desmethylsimmondsin.

In another particularly preferred embodiment, the compounds according to the invention is represented by formula (I) wherein $R_4$ is —OH and $R_5$ is —OCH$_3$, wherein $R_3$, $R_3'$ $R_4'$, and $R_6'$ are —OH, and wherein $R_2'$ is ferulate. Said compound is referred to as 4-desmethylsimmondsin-2'-ferulate.

In yet another preferred embodiment, the compounds according to the invention are represented by formula (I) wherein $R_4$ and $R_5$ are —$OCH_3$ and wherein $R_3$, $R_2'$, $R_3'$ $R_4'$, and $R_6'$ are independently selected from the group comprising hydroxyl or an ester as defined above.

In a particularly preferred embodiment, the compound according to the invention is represented by formula (I) wherein $R_4$ and $R_5$ are —$OCH_3$, and wherein $R_3$, $R_2'$, $R_3'$ $R_4'$, and $R_6'$ are —OH. Said compound is referred to as 4,5-dimethylsimmondsin.

In another particularly preferred embodiment, the compounds according to the invention is represented by formula (I) wherein $R_4$ and $R_5$ are —$OCH_3$, wherein $R_3R_3'$ $R_4'$, and $R_6'$ are —OH, and wherein $R_2'$ is ferulate. Said compound is referred to as 4,5-dimethylsimmondsin-2' ferulate.

Table 1 provides examples of different compounds according to the invention, which naturally occur in jojoba.

TABLE 1

| $R_4$ | $R_5$ | $R_3$ | $R_2'$ | $R_3'$ | $R_4'$ | $R_6'$ |
|---|---|---|---|---|---|---|
| —OH | —OH | —OH | —OH | —OH | —OH | —OH |
| —OH | —OH | —OH | -ferulate | —OH | —OH | —OH |
| —$OCH_3$ | —OH | —OH | —OH | —OH | —OH | —OH |
| —$OCH_3$ | —OH | —OH | -ferulate | —OH | —OH | —OH |
| —OH | —$OCH_3$ | —OH | —OH | —OH | —OH | —OH |
| —OH | —$OCH_3$ | —OH | -ferulate | —OH | —OH | —OH |
| —$OCH_3$ | —$OCH_3$ | —OH | —OH | —OH | —OH | —OH |
| —$OCH_3$ | —$OCH_3$ | —OH | -ferulate | —OH | —OH | —OH |

Additional non-limiting examples of compounds according to the invention having general formula (I) are listed hereunder in Table 2.

TABLE 2

Formula (I)

| $R_4$ | $R_5$ | $R_3$ | $R_2'$ | $R_3'$ | $R_4'$ | $R_6'$ |
|---|---|---|---|---|---|---|
| —H | —OH | —OH | —OH | —OH | —OH | —OH |
| —$CH_3$ | —OH | —OH | —OH | —OH | —OH | —OH |
| —COOH | —OH | —OH | —OH | —OH | —OH | —OH |
| —CH=$CH_2$ | —OH | —OH | —OH | —OH | —OH | —OH |
| —$CO_2CH_3$ | —OH | —OH | —OH | —OH | —OH | —OH |
| —$OC_2H_5$ | —OH | —OH | —OH | —OH | —OH | —OH |
| —$OC_3H_7$ | —OH | —OH | —OH | —OH | —OH | —OH |
| —$CO_2C_2H_5$ | —OH | —OH | —OH | —OH | —OH | —OH |
| —CHO | —OH | —OH | —OH | —OH | —OH | —OH |
| —$CH_2OH$ | —OH | —OH | —OH | —OH | —OH | —OH |
| —$CHOHCH_3$ | —OH | —OH | —OH | —OH | —OH | —OH |
| —$CH_2$—$CH_2$—CH=$CH_2$ | —OH | —OH | —OH | —OH | —OH | —OH |
| —$COOCH_3$ | —OH | —OH | —OH | —OH | —OH | —OH |
| —$CH_2OCH_3$ | —OH | —OH | —OH | —OH | —OH | —OH |
| —$CH_2OCH_2CH_3$ | —OH | —OH | —OH | —OH | —OH | —OH |
| —$CH_2SCH_3$ | —OH | —OH | —OH | —OH | —OH | —OH |
| ethyl acetate group | —OH | —OH | —OH | —OH | —OH | —OH |
| acetone group | —OH | —OH | —OH | —OH | —OH | —OH |
| butan-2-one group | —OH | —OH | —OH | —OH | —OH | —OH |
| ethyl succinate group | —OH | —OH | —OH | —OH | —OH | —OH |
| 2-hydroxypropyl group | —OH | —OH | —OH | —OH | —OH | —OH |

TABLE 2-continued

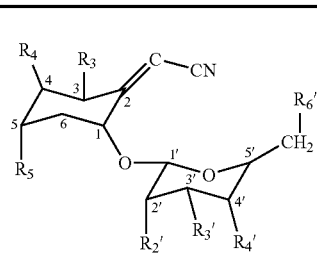

Formula (I)

| R$_4$ | R$_5$ | R$_3$ | R$_2'$ | R$_3'$ | R$_4'$ | R$_6'$ |
|---|---|---|---|---|---|---|
| OH–CH(–)–CH$_2$–CH$_3$ (2-pentyl) | —OH | —OH | —OH | —OH | —OH | —OH |
| —OH | —H | —OH | ester | —OH | —OH | —OH |
| —OH | —CH$_3$ | —OH | ester | —OH | —OH | —OH |
| —OH | —COOH | —OH | ester | —OH | —OH | —OH |
| —OH | —CH=CH$_2$ | —OH | ester | —OH | —OH | —OH |
| —OH | —CO$_2$CH$_3$ | —OH | ester | —OH | —OH | —OH |
| —OH | —OC$_2$H$_5$ | —OH | ester | —OH | —OH | —OH |
| —OH | —OC$_3$H$_7$ | —OH | ester | —OH | —OH | —OH |
| —OH | —CO$_2$C$_2$H$_5$ | —OH | ester | —OH | —OH | —OH |
| —OH | —CHO | —OH | ester | —OH | —OH | —OH |
| —OH | —CH$_2$OH | —OH | ester | —OH | —OH | —OH |
| —OH | —CHOHCH$_3$ | —OH | ester | —OH | —OH | —OH |
| —OH | —CH$_2$—CH$_2$—CH=CH$_2$ | —OH | ester | —OH | —OH | —OH |
| —OH | —COOCH$_3$ | —OH | ester | —OH | —OH | —OH |
| —OH | —CH$_2$OCH$_3$ | —OH | ester | —OH | —OH | —OH |
| —OH | —CH$_2$OCH$_2$CH$_3$ | —OH | ester | —OH | —OH | —OH |
| —OH | —CH$_2$SCH$_3$ | —OH | ester | —OH | —OH | —OH |
| —OH | ethyl acetate group | —OH | ester | —OH | —OH | —OH |
| —OH | acetone group | —OH | ester | —OH | —OH | —OH |
| —OH | 2-pentanone group | —OH | ester | —OH | —OH | —OH |
| —OH | ethyl succinate group | —OH | ester | —OH | —OH | —OH |
| —OH | isopropanol group | —OH | ester | —OH | —OH | —OH |
| —OH | 2-pentanol group | —OH | ester | —OH | —OH | —OH |
| —OH | —H | —OH | ferulate | —OH | —OH | —OH |
| —OH | —CH$_3$ | —OH | ferulate | —OH | —OH | —OH |
| —OH | —COOH | —OH | ferulate | —OH | —OH | —OH |
| —OH | —CH=CH$_2$ | —OH | ferulate | —OH | —OH | —OH |
| —OH | —CO$_2$CH$_3$ | —OH | ferulate | —OH | —OH | —OH |
| —OH | —OC$_2$H$_5$ | —OH | ferulate | —OH | —OH | —OH |
| —OH | —CO$_3$H$_7$ | —OH | ferulate | —OH | —OH | —OH |
| —OH | —CO$_2$C$_2$H$_5$ | —OH | ferulate | —OH | —OH | —OH |
| —OH | —CHO | —OH | ferulate | —OH | —OH | —OH |
| —OH | —CH$_2$OH | —OH | ferulate | —OH | —OH | —OH |
| —OH | —CHOHCH$_3$ | —OH | ferulate | —OH | —OH | —OH |

TABLE 2-continued

Formula (I)

| R$_4$ | R$_5$ | R$_3$ | R$_2$' | R$_3$' | R$_4$' | R$_6$' |
|---|---|---|---|---|---|---|
| —OH | —CH$_2$—CH$_2$—CH=CH$_2$ | —OH | ferulate | —OH | —OH | —OH |
| —OH | —COOCH$_3$ | —OH | ferulate | —OH | —OH | —OH |
| —OH | —CH$_2$OCH$_3$ | —OH | fewlate | —OH | —OH | —OH |
| —OH | —CH$_2$OCH$_2$CH$_3$ | —OH | ferulate | —OH | —OH | —OH |
| —OH | —CH$_2$SCH$_3$ | —OH | ferulate | —OH | —OH | —OH |
| —OH | —O—C(=O)—CH$_3$ (ethyl acetate group) | —OH | ferulate | —OH | —OH | —OH |
| —OH | —C(=O)—CH$_3$ (acetone group) | —OH | ferulate | —OH | —OH | —OH |
| —OH | —C(=O)—CH$_2$CH$_2$CH$_3$ | —OH | ferulate | —OH | —OH | —OH |
| —OH | —O—C(=O)—CH$_2$CH$_2$COOH | —OH | ferulate | —OH | —OH | —OH |
| —OH | —CH(OH)CH$_3$ | —OH | ferulate | —OH | —OH | —OH |
| —OH | —CH(OH)CH$_2$CH$_2$CH$_3$ | —OH | ferulate | —OH | —OH | —OH |
| —OH | —OH | —OH | ferulate | —OH | —OH | —OH |
| —OCH$_3$ | —OH | —OH | ferulate | —OH | —OH | —OH |
| —OH | —OCH$_3$ | —OH | ferulate | —OH | —OH | —OH |
| —OCH$_3$ | —OCH$_3$ | —OH | ferulate | —OH | —OH | —OH |
| —CH$_3$ | —OH | —OH | ferulate | —OH | —OH | —OH |
| —COOH | —OH | —OH | ferulate | —OH | —OH | —OH |
| —CH$_2$OH | —OH | —OH | ferulate | —OH | —OH | —OH |
| —OC$_2$H$_5$ | —OH | —OH | ferulate | —OH | —OH | —OH |
| —CH$_3$ | —OCH$_3$ | —OH | ferulate | —OH | —OH | —OH |
| —COOH | —OCH$_3$ | —OH | ferulate | —OH | —OH | —OH |
| —CH$_2$OH | —OCH$_3$ | —OH | ferulate | —OH | —OH | —OH |
| —OC$_2$H$_5$ | —OCH$_3$ | —OH | ester | —OH | —OH | —OH |
| —OH | —CH$_3$ | —OH | ester | —OH | —OH | —OH |
| —OH | —COOH | —OH | ester | —OH | —OH | —OH |
| —OH | —CH$_2$OH | —OH | ester | —OH | —OH | —OH |
| —OH | —OC$_2$H$_5$ | —OH | ester | —OH | —OH | —OH |
| —OCH$_3$ | —CH$_3$ | —OH | ester | —OH | —OH | —OH |
| —OCH$_3$ | —COOH | —OH | ester | —OH | —OH | —OH |
| —OCH$_3$ | —CH$_2$OH | —OH | ester | —OH | —OH | —OH |
| —OCH$_3$ | —OC$_2$H$_5$ | —OH | ester | —OH | —OH | —OH |
| —CH$_3$ | —CH$_3$ | —OH | ester | —OH | —OH | —OH |
| —COOH | —COOH | —OH | ester | —OH | —OH | —OH |
| —CH$_2$OH | —CH$_2$OH | —OH | ester | —OH | —OH | —OH |
| —OC$_2$H$_5$ | —OC$_2$H$_5$ | —OH | ester | —OH | —OH | —OH |
| —OH | —OH | —OH | ferulate | —OH | ferulate | —OH |
| —OCH$_3$ | —OH | —OH | ferulate | —OH | ferulate | —OH |
| —OH | —OCH$_3$ | —OH | ferulate | —OH | ferulate | —OH |

TABLE 2-continued

Formula (I)

| $R_4$ | $R_5$ | $R_3$ | $R_2'$ | $R_3'$ | $R_4'$ | $R_6'$ |
|---|---|---|---|---|---|---|
| —$OCH_3$ | —$OCH_3$ | —OH | ferulate | —OH | ferulate | —OH |
| —$CH_3$ | —OH | —OH | ferulate | —OH | ferulate | —OH |
| —COOH | —OH | —OH | ferulate | —OH | ferulate | —OH |
| —$CH_2OH$ | —OH | —OH | ferulate | —OH | ferulate | —OH |
| —$OC_2H_5$ | —OH | —OH | ferulate | —OH | ferulate | —OH |
| —$CH_3$ | —$OCH_3$ | —OH | ferulate | —OH | ferulate | —OH |
| —COOH | —$OCH_3$ | —OH | ferulate | —OH | ferulate | —OH |
| —$CH_2OH$ | —$OCH_3$ | —OH | ferulate | —OH | ferulate | —OH |
| —$OC_2H_5$ | —$OCH_3$ | —OH | ferulate | —OH | ferulate | —OH |
| —OH | —$CH_3$ | —OH | ester | —OH | ester | —OH |
| —OH | —COOH | —OH | ester | —OH | ester | —OH |
| —OH | —$CH_2OH$ | —OH | ester | —OH | ester | —OH |
| —OH | —$OC_2H_5$ | —OH | ester | —OH | ester | —OH |
| —$OCH_3$ | —$CH_3$ | —OH | ester | —OH | ester | —OH |
| —$OCH_3$ | —COOH | —OH | ester | —OH | ester | —OH |
| —$OCH_3$ | —$CH_2OH$ | —OH | ester | —OH | ester | —OH |
| —$OCH_3$ | —$OC_2H_5$ | —OH | ester | —OH | ester | —OH |
| —$CH_3$ | —$CH_3$ | —OH | ester | —OH | ester | —OH |
| —COOH | —COOH | —OH | ester | —OH | ester | —OH |
| —$CH_2OH$ | —$CH_2OH$ | —OH | ester | —OH | ester | —OH |
| —$OC_2H_5$ | —$OC_2H_5$ | —OH | ester | —OH | ester | —OH |
| —OH | —OH | —OH | ferulate | ferulate | ferulate | —OH |
| —$OCH_3$ | —OH | —OH | ferulate | ferulate | ferulate | —OH |
| —OH | —$OCH_3$ | —OH | ferulate | ferulate | ferulate | —OH |
| —$OCH_3$ | —$OCH_3$ | —OH | ferulate | ferulate | ferulate | —OH |
| —$CH_3$ | —OH | —OH | ferulate | ferulate | ferulate | —OH |
| —OOOH | —OH | —OH | ferulate | ferulate | ferulate | —OH |
| —$CH_2OH$ | —OH | —OH | ferulate | ferulate | ferulate | —OH |
| —$OC_2H_5$ | —OH | —OH | ferulate | ferulate | ferulate | —OH |
| —$CH_3$ | —$OCH_3$ | —OH | ferulate | ferulate | ferulate | —OH |
| —COOH | —$OCH_3$ | —OH | ferulate | ferulate | ferulate | —OH |
| —$CH_2OH$ | —$OCH_3$ | —OH | ferulate | ferulate | ferulate | —OH |
| —$OC_2H_5$ | —$OCH_3$ | —OH | ferulate | ferulate | ferulate | —OH |
| —OH | —$CH_3$ | —OH | ester | ester | ester | —OH |
| —OH | —COOH | —OH | ester | ester | ester | —OH |
| —OH | —$CH_2OH$ | —OH | ester | ester | ester | —OH |
| —OH | —$OC_2H_5$ | —OH | ester | ester | ester | —OH |
| —$OCH_3$ | —$CH_3$ | —OH | ester | ester | ester | —OH |
| —$OCH_3$ | —COOH | —OH | ester | ester | ester | —OH |
| —$OCH_3$ | —$CH_2OH$ | —OH | ester | ester | ester | —OH |
| —$OCH_3$ | —$CO_2H_5$ | —OH | ester | ester | ester | —OH |
| —$CH_3$ | —$CH_3$ | —OH | ester | ester | ester | —OH |
| —COOH | —COOH | —OH | ester | ester | ester | —OH |
| —$CH_2OH$ | —$CH_2OH$ | —OH | ester | ester | ester | —OH |
| —$CO_2H_5$ | —$OC_2H_5$ | —OH | ester | ester | ester | —OH |

In another preferred embodiment according to the invention, the simmondsin according to the invention is selected from the group comprising dimethylsimmondsin, desmethylsimmondsin, didesmethylsimmondsin, stereoisomeric forms, racemic mixtures, metabolites, esters or salts thereof, or mixtures thereof.

In a more preferred embodiment, the simmondsin according to the invention is selected from the group comprising 4-desmethylsimmondsin, 5-desmethylsimmondsin, 4,5-didesmethylsimmondsin, 4,5-dimethylsimmondsin stereoisomeric forms, racemic mixtures, metabolites, esters or salts thereof, or mixtures thereof.

In another more preferred embodiment, the simmondsin according to the invention is selected from the group comprising 4-desmethylsimmondsin, 5-desmethylsimmondsin, 4,5-didesmethylsimmondsin, 4-desmethylsimmondsin-2'-ferulate, 5-desmethylsimmondsin-2'-ferulate, 4,5-didesmethylsimmondsin-2'-ferulate, 4,5-dimethylsimmondsin-2'-ferulate, or any mixtures thereof.

In another preferred embodiment, the invention relates to compounds having general formula (I), which have a high apolar character. Polarity may greatly determine the biological activity of the simmondsin compounds according to the present invention. In particular, compounds having general formula (I) having apolar character may be obtained by providing esters of compounds according to the present invention.

In yet another embodiment the invention relates to a compound having general formula (I) as defined above.

It has now surprisingly been found that active components as defined above, and in particular compounds having formula (I) according to the present invention, have a potent angiogenesis-inhibiting effect. According to the present invention the terms "anti-angiogenesis activity" or "angiogenesis-inhibiting" are defined herein as the ability of the compounds as defined in the present invention to inhibit, prevent, or greatly reduce the formation or outgrowth of blood or lymph vessels, or destroy such vessels during sprouting or outgrowth in vitro as well as in vivo.

In another embodiment, active components according to the present invention, and in particular compounds having formula (I) according to the present invention, have a specific angiogenesis-inhibiting effect on one or more of the specific steps in the angiogenesis process. The complete angiogenesis process includes different steps. Endothelial cells, the cells that form the walls of blood vessels, are the source of new blood vessels and have a great ability to divide and travel. The construction of a vascular network requires different sequential steps including:
1. the release of proteases from "activated" endothelial cells
2. degradation of the basement membrane surrounding the existing vessel
3. migration of the endothelial cells into the interstitial space
4. endothelial cell proliferation
5. tube formation and the subsequent lumen formation
6. generation of new basement membrane with the recruitment of pericytes
7. fusion of the newly formed vessels
8. initiation of blood flow.

Advantageously, different compounds according to this invention show quantitative and qualitative differences on certain steps involved in the angiogenesis process.

Furthermore, it was also demonstrated that active components, and in particular compounds having formula (I) according to the present invention, have anti-tumor activity.

In addition, it was surprisingly shown that active components according to the present invention, and in particular compounds having formula (I) according to the present invention, have low levels of cytotoxicity. This means that these compounds do not induce significant detrimental effect(s) on healthy cells, tissues or organs. It has been shown that the compounds according to the invention do not show a relevant cytotoxic effect on healthy tissues in vitro (see examples).

Another surprising characteristic of active components according to the present invention is that the components show no significant oestrogen-like activity (see example 7).

In view of these interesting properties, active components according to the invention are particularly useful in medical applications. Therefore, in a preferred embodiment, the present invention relates to the use of an active component derived from jojoba for the manufacture of a medicament for inhibiting angiogenesis. In a preferred embodiment, the invention relates to the use of a simmondsin, as defined above, stereoisomeric forms, racemic mixtures, metabolites, esters or salts thereof, or mixtures thereof for the manufacture of a medicament for inhibiting angiogenesis.

The angiogenesis-inhibiting properties of active components according to the present invention are preferably due to simmondsins selected from the group comprising as desmethyl- and didesmethylsimmondsin and their respective ferulates. It has been demonstrated that inhibiting properties of these compounds can not only be obtained after oral administration but also by direct contact with growing cells as revealed by in vitro assays (see examples). Furthermore, dimethylsimmondsin ferulates show a significant angiogenesis-inhibiting activity, which is higher than the activity of unsubstituted dimethylsimmondsin.

The term "angiogenesis" or "neovascularisation" are used herein as synonyms and refer to the proliferation and formation of new blood vessels from existing blood vessels. Blood vessel formation is required for normal tissue growth, placental and embryonic development, wound healing, etc. . . .

Angiogenesis also plays an important role in several diseases. Angiogenesis is also very important in the development of many malignancies in colon, breasts, endometrium, ovary, cervix, prostate and other tissues. Since the present invention provides compounds useful for inhibiting angiogenesis, these compounds are also particularly suitable for treating diseases that result from unwanted or uncontrolled angiogenesis activity. The present invention therefore relates in another embodiment to the use of an active component derived from jojoba for the manufacture of a medicament for treating angiogenesis-related diseases. Further provided in the present invention is the use of a simmondsin, as defined above, or stereoisomeric forms, racemic mixtures, metabolites, esters or salts thereof, or mixtures thereof, for the manufacture of a medicament for treating angiogenesis-related diseases. In a more preferred embodiment, said simmondsin naturally occurs in jojoba and is comprised within jojoba flour or a jojoba extract.

In a more preferred embodiment, said simmondsin, as defined above, or stereoisomeric forms, racemic mixtures, metabolites, esters or salts thereof, or mixtures thereof, used for the manufacture of a medicament for inhibiting angiogenesis or for treating angiogenesis-related diseases naturally occurs in jojoba or is comprised within jojoba flour or a jojoba extract.

In another preferred embodiment, said simmondsin is selected from the group comprising 4-desmethylsimmondsin, 5-desmethylsimmondsin, 4,5-didesmethylsimmondsin, 4,5-dimethylsimmondsin, 4-desmethylsimmondsin-2'-ferulate, 5-desmethylsimmondsin-2'-ferulate, 4,5-didesmethylsimmondsin-2'-ferulate, 4,5-dimethylsimmondsin-2'-ferulate, and any mixtures thereof.

In another preferred embodiment, said simmondsin is selected from the group comprising 4-desmethylsimmondsin, 5-desmethylsimmondsin, 4,5-didesmethylsimmondsin, 4,5-dimethylsimmondsin, or stereoisomeric forms, racemic mixtures, metabolites, esters or salts thereof, or mixtures thereof.

In yet another preferred embodiment, the simmondsin is selected from the group comprising 4-desmethylsimmondsin, 5-desmethylsimmondsin, 4,5-didesmethylsimmondsin, 4-desmethylsimmondsin-2'-ferulate, 5-desmethylsimmondsin-2'-ferulate, 4,5-didesmethylsimmondsin-2'-ferulate, 4,5-dimethylsimmondsin-2'-ferulate, and any mixtures thereof.

The term "angiogenesis-related diseases" as used herein refers to diseases wherein angiogenesis, as defined herein, plays a crucial detrimental role. Angiogenesis-related diseases are chosen from the following non-limiting list comprising cancer, hemangiomas, the formation of atherosclerotic plaques, inflammatory diseases, arthritis, psoriasis, pre-eclampsia, intrauterine growth retardation, endometriosis, fibrosis of the liver and of the kidney, certain pathologies as a result of diabetes, eye-diseases in which abnormal vessels proliferate and destroy vision, such as proliferative retinopathy, aged-related maculopahty (as a result of diabetes mellitus), diabetic retinopathy, macular degeneration, neovascular glaucoma, retrolental fibroplasias, retinal vascularisation, etc. . . .

In another preferred embodiment the invention relates to the use of an active component derived from jojoba for the manufacture of a medicament for treating cancer. The invention in particular relates to the use of a simmondsin, as defined above, or stereoisomeric forms, racemic mixtures, metabolites, esters or salts thereof, or mixtures thereof, for the manufacture of a medicament for treating cancer.

Cancers which may be treated according to the present invention comprise but are not limited to solid tumors or metastasis. Metastasis is the form of cancer wherein the transformed or malignant cells are traveling and spreading the cancer from one organ to another. The cancer can be of the skin, breast, brain, cervical carcinomas, testicular carcinomas, etc. More particularly, cancers may include, but are not limited to the following organs or systems: cardiac, lung, gastrointestinal, genitourinary tract, liver, bone, nervous system, gynecological, hematologic, skin, and adrenal glands. More particularly, the methods herein can be used for treating gliomas (Schwannoma, glioblastoma, astrocytoma), melanoma, neuroblastoma, pheochromocytoma, paraganlioma, meningioma, adrenalcortical carcinoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia.

Angiogenesis is of particular interest in the metastasis of tumorigenic cancers. De novo capillary production is a crucial event in tumor growth and metastasis since the cells in solid tumors must receive the necessary oxygen and nutrients to survive and grow. In particular, it is known to the skilled physician that tumors depending on angiogenesis represent a large number of the existing cancers. Indeed, tumors produce angiogenetic factors to induce formation of new blood vessels (Folkman, 2002; Semin Oncol 29 (6 Suppl 16):15-18). Inhibition of blood vessel development results in restricted energy supply to the tumor, thus causing an arrest in its development and hence, the start of its regression.

In view of the effects of angiogenesis in cancer development, the present invention provides compounds, having anti-angiogenesis activity, which may also be, very useful in the treatment of cancers depending on angiogenesis. The term "cancer depending on angiogenesis" as used herein refers to cancers in which angiogenesis plays a crucial and detrimental role. Therefore, in a preferred embodiment the present invention relates to the use of an active component derived from jojoba for the manufacture of a medicament for treating cancer depending on angiogenesis. The invention in particular relates to the use of a simmondsin, as defined above, or stereoisomeric forms, racemic mixtures, metabolites, esters or salts thereof, or mixtures thereof, used for the manufacture of a medicament for treating cancer depending on angiogenesis.

Recent studies also suggest angiogenesis inhibiting compounds to be effective in new drug development for the treatment of other diseases wherein uncontrolled blood vessel growth and (synovial) inflammation is involved such as rheumatoid arthritis (Bodolay et al., 2002), psoriasis (Xia et al., 2003; Blood 20) and hypoxia-induced retinal neovascularization (Takagi et al., 2003, Ophtalmol. Vis Sci. 44(I): 393402). Therefore, a lot of research is directed to obtain a useful angiogenesis inhibitor (Van Hinsbergh et al., 1999, Ann. Oncol. 1999, 10 (Suppl 4):60-63; O'Reilly, 2003, Methods Mol. Biol. 223:599-634).

In another embodiment the invention therefore relates to the use of an active component derived from jojoba for the manufacture of a medicament for treating arthritis. The invention in particular relates to the use of a simmondsin, as defined above, or stereoisomeric forms, racemic mixtures, metabolites, esters or salts thereof, or mixtures thereof, for the manufacture of a medicament for treating arthritis. The term "arthritis" as used herein, is meant to encompass all forms of joint inflammation and comprises, but is not limited to osteoarthritis, rheumatoid arthritis, ankylosing spondylitis, bursitis, fibromyalgia, gout, infectious arthritis, juvenile rheumatoid arthritis, psoriatic arthritis, reactive arthritis, scleroderma, systemic lupus erythematosus (SLE), tendonitis, synovitis, etc. . . .

Furthermore, according to another embodiment, the invention relates to the use of an active component derived from jojoba for the manufacture of a medicament for treating psoriaris. The invention in particular relates to the use of a simmondsin, as defined above, or stereoisomeric forms, racemic mixtures, metabolites, esters or salts thereof, or mixtures thereof, for the manufacture of a medicament for treating psoriaris. The term "psoriasis" is defined as being a chronic skin disease characterized by scaling and inflammation and is meant to encompass, as used herein, all forms of psoriasis, including but not limited to plaque psoriasis, guttate psoriasis, pustular psoriasis, inverse psoriasis, erythrodermic psoriasis, etc . . .

Since angiogenesis-inhibition plays a role in placental and embryonic development, the present active components can also be used, according to another preferred embodiment, for contraceptive and abortive purposes. Therefore, in another preferred embodiment, the invention relates to the use of an active component derived from jojoba for the manufacture of a medicament having a contraceptive or abortive effect. The invention in particular relates to the use of a simmondsin, as defined above, or stereoisomeric forms, racemic mixtures, metabolites, esters or salts thereof, or mixtures thereof, for the manufacture of a medicament having a contraceptive or abortive effect.

Furthermore, VEGF, which plays a key role in angiogenesis, has been reported to be involved in spermatogenesis. Therefore, the present active components can also be used, according to another preferred embodiment, for controlling male potency. Therefore, in another preferred embodiment, the invention relates to the use of an active component derived from jojoba for the manufacture of a medicament for controlling male potency. The invention in particular relates to the use of a simmondsin, as defined above, or stereoisomeric forms, racemic mixtures, metabolites, esters or salts thereof, or mixtures thereof, for the manufacture of a medicament for controlling male potency.

In yet another embodiment the invention relates to the use of a simmondsin having general formula (I), as defined above, as a medicament. In particular the present invention relates to the use of a simmondsin having general formula (I), as defined above, with the exception of 4,5-dimethylsimmondsin as a medicament. In addition, the present invention relates to the use of a simmondsin having general formula (I), as defined above, with the exception of 4,5-dimethylsimmondsin-2'-ferulate as a medicament. Preferably, the invention relates to the use of 4-desmethylsimmondsin, 5-desmethylsimmondsin, 4,5-didesmethylsimmondsin, 4-desmethylsimmondsin-2'- ferulate, 5-desmethylsimmondsin-2'-ferulate, 4,5-didesmethylsimmondsin-2'-ferulate, and any mixtures thereof as a medicament.

The present invention further relates to an extract from jojoba or jojoba flour for use as a medicament. In particular, the invention relates to an extract from jojoba or jojoba flour for use as a medicament, whereby the flour or the extract are substantially free of 4,5-dimethylsimmondsin. In addition, the invention relates to an extract from jojoba or jojoba flour for use as a medicament, whereby the flour or the extract are substantially free of 4,5-dimethylsimmondsin-2'-ferulate.

An active component according to the invention, and in particular a simmondsin as defined above, or stereoisomeric forms, racemic mixtures, metabolites, esters or salts thereof, or mixtures thereof, can be applied to animals, preferably mammals, and in particular humans as pharmaceuticals per se, in mixtures with one another or in the form of pharmaceutical preparations.

Therefore, in another embodiment, the invention relates to a pharmaceutical composition comprising a therapeutically effective amount of an active component derived from jojoba and a pharmaceutical acceptable excipient.

The invention also relates to a pharmaceutical composition comprising a therapeutically effective amount of a simmondsin, as defined above, or stereoisomeric forms, racemic mixtures, metabolites, esters or salts thereof, or mixtures thereof and a pharmaceutical acceptable excipient.

The present invention thus relates to pharmaceutical preparations, which as active constituents contains an effective dose of at least one of the active components as defined above in addition to customary pharmaceutically innocuous excipients and auxiliaries. The pharmaceutical composition may in particular comprise jojoba flour, an extract thereof or any of the above-mentioned compounds having general formula (I) and stereoisomeric forms, racemic mixtures, metabolites, esters, or salts thereof, as well as any mixtures thereof. The pharmaceutical composition may thus comprise mixtures of jojoba flour and a compound of formula (I), jojoba flour and salts or esters of a compound of formula (I), etc . . . or any other combination.

In another embodiment the invention relates to a pharmaceutical composition comprising a therapeutically effective amount of a simmondsin, as defined above, or stereoisomeric forms, racemic mixtures, metabolites, esters or salts thereof, or mixtures thereof, with the exception of 4,5-dimethylsimmondsin or 4,5-dimethylsimmondsin-2'-ferulate, and a pharmaceutical acceptable excipient.

The term "therapeutically effective amount" as used herein means that amount of active component(s) or pharmaceutical agent that elicits the biological or medicinal response in a tissue, system, animal or human that is being sought by a researcher, veterinarian, medical doctor or other clinician, which includes alleviation of the symptoms of the disease being treated.

The pharmaceutical preparations normally contain 0.1 to 90% by weight of active components according to the invention. The pharmaceutical preparations can be prepared in a manner known per se to a person skilled in the art. For this purpose, at least one active component according to the invention, together with one or more solid or liquid pharmaceutical excipients and/or auxiliaries and, if desired, in combination with other pharmaceutical active components, are brought into a suitable administration form or dosage form which can then be used as a pharmaceutical in human medicine or veterinary medicine.

The person skilled in the art is familiar on the basis of his expert knowledge with the excipient or auxiliaries that are suitable for the desired pharmaceutical formulation. Beside solvents, gel-forming agents, suppository bases, tablet auxiliaries and other active compound carriers, antioxidants, dispersants, emulsifiers, antifoams, flavour corrigents, preservatives, solubilizers, agents for achieving a depot effect, buffer substances or colorants are also useful.

In a preferred embodiment the administration route of a pharmaceutical composition according to the present invention is without limitation an oral route, a topical route or a parenteral route.

Particular administration forms of the pharmaceutical composition may be, for example, solutions, suspensions, emulsions, creams, tablets, capsules, nasal sprays, liposomes or micro-reservoirs, especially compositions in orally ingestible or sterile injectable form, for example, as sterile injectable aqueous or oleaginous suspensions or suppositories. The preferred form of composition contemplated is the dry solid form, which includes capsules, granules, tablets, pills, boluses and powders. The solid carrier may comprise one or more excipients, e.g. lactose, fillers, disintegrating agents, binders, e.g. cellulose, carboxymethylcellulose or starch or anti-stick agents, e.g. magnesium stearate, to prevent tablets from adhering to tabletting equipment. Tablets, pills and boluses may be formed so as to disintegrate rapidly or to provide slow release of the active ingredient.

The pharmaceutical compositions of this invention can be administered to humans or animals in dosage ranges specific for each component comprised in said compositions. The component comprised in said composition can be administered together or separately. It will be understood, however, that specific dose level and frequency of dosage for any particular patient may be varied and will depend upon a variety of factors including the activity of the specific active component employed, the metabolic stability and length of action of that compound, the age, body weight, general health, sex, diet, mode and time of administration, rate of excretion, drug combination, the severity of the particular condition, and the host undergoing therapy.

According to one embodiment the pharmaceutical composition according to the invention is formulated to be applied orally to humans and animals. The present pharmaceutical composition can for instance by applied orally for the treatment of tumors or other angiogenesis-related diseases accessible through oral administration.

Preferably, said pharmaceutical composition is formulated for an oral administration and comprises jojoba flour, and preferably in a concentration of 80 per cent by weight or lower, preferably in a concentration of 60 per cent by weight or lower, more preferably in a concentration of 40 per cent by weight or lower and more preferably in a concentration of 20 per cent by weight or lower. It is clear that the concentration depends on the physical activity of adjuvants in the composition such as e.g. emulsifiers.

Said pharmaceutical composition can also be formulated for an oral administration and comprises an extract from jojoba flour or substances isolated thereof comprising a simmondsin as defined above or stereoisomeric forms, racemic mixtures, metabolites, esters or salts thereof, or mixtures thereof, in a therapeutic effective amount, and preferably in a concentration of 5 per cent by weight or lower, preferably in a concentration of 3 per cent by weight or lower, and more preferably in a concentration of 1 per cent by weight or lower, and even more preferably in a concentration of 0.15 per cent by weight or lower. The therapeutic effective amount depends on the disease to be treated and the professional skill of a therapist.

According to another embodiment, the pharmaceutical composition according to the invention is formulated to be applied parenterally to humans and animals. The present pharmaceutical composition can by applied parenterally for the treatment of tumors or other angiogenesis-related diseases accessible through parenteral administration.

According to a particularly preferred embodiment, said pharmaceutical composition is formulated for parenteral administration and comprises an extract from jojoba flour, or a simmondsin as defined above or stereoisomeric forms, racemic mixtures, metabolites, esters or salts thereof, or mixtures thereof, in a therapeutic effective amount and preferably in a concentration of 5 per cent by weight or lower, preferably in a concentration of 3 per cent by weight or lower, and more preferably in a concentration of 1 per cent by weight or lower, and even more preferably in a concentration of 0.15 per cent by weight or lower. The therapeutic effective amount depends on the disease to be treated and the professional skill of a therapist.

In yet another embodiment, the pharmaceutical composition according to the invention is formulated to be applied topically. The present pharmaceutical composition can for instance by applied topically for the treatment of tumors or other angiogenesis-related diseases accessible through a topical application on the skin of humans and animals. Preferably, said pharmaceutical composition is formulated for a topical application on the skin and comprises an extract from jojoba flour, or substances isolated thereof comprising a simmondsin as defined above or stereoisomeric forms, racemic mixtures, metabolites, esters or salts thereof, or mixtures thereof, in a therapeutic effective amount and preferably in a concentration ranging between 0.1 and 10 per cent by weight, and preferably between 0.5 and 5 per cent by weight. The therapeutic effective amount depends on the disease to be treated and the professional skill of a therapist.

Due to their favourable pharmacological, in particular their angiogenesis-inhibiting properties, active components according to the invention are useful in a treatment of diseases wherein inhibition of angiogeneises is required and in the treatment of individuals suffering from an angiogenesis-related disease. Therefore, in another embodiment, the invention relates to a method of inhibiting angiogenesis in humans and animals comprising administering to the human or animal In need thereof a therapeutically effective amount of an active component derived from jojoba according to the invention. In particular the invention relates to a method of inhibiting angiogenesis in humans and animals comprising administering to the human or animal in need thereof a therapeutically effective amount of a simmondsin as defined above or stereoisomeric forms, racemic mixtures, metabolites, esters or salts thereof, or mixtures thereof.

The invention further provides in another preferred embodiment, a method of treating angiogenesis-related diseases in humans and animals comprising administering to the human or animal in need thereof a therapeutically effective amount of an active component derived from jojoba according to the invention. In particular, the invention provides a method of treating angiogenesis-related diseases, comprising administering to the human or animal in need thereof a therapeutically effective amount of a therapeutically effective amount of a simmondsin as defined above or stereoisomeric forms, racemic mixtures, metabolites, esters or salts thereof, or mixtures thereof.

In a particularly preferred embodiment, the invention provides a method for treating a cancer depending on angiogenesis, comprising administering to the human or animal in need thereof a therapeutically effective amount of an active component derived from jojoba according to the invention, and in particular of a simmondsin as defined above or stereoisomeric forms, racemic mixtures, metabolites, esters or salts thereof, or mixtures thereof.

In another preferred embodiment, the invention provides a method for treating all forms of arthritis comprising administering to the human or animal in need thereof a therapeutically effective amount of an active component derived from jojoba according to the invention, and in particular of a simmondsin as defined above or stereoisomeric forms, racemic mixtures, metabolites, esters or salts thereof, or mixtures thereof.

In yet another preferred embodiment, the invention provides a method for treating psoriasis comprising administering to the human or animal in need thereof a therapeutically effective amount of an active component derived from jojoba according to the invention, and in particular of a simmondsin as defined above or stereoisomeric forms, racemic mixtures, metabolites, esters or salts thereof, or mixtures thereof.

In a further preferred embodiment, the invention provides a method for contraception or an abortive method comprising administering to the human or animal in need thereof a therapeutically effective amount of an active component derived from jojoba according to the invention, and in particular of a simmondsin as defined above or stereoisomeric forms, racemic mixtures, metabolites, esters or salts thereof, or mixtures thereof.

In another further preferred embodiment, the invention provides a method for controlling male potency comprising administering to the human or animal in need thereof a therapeutically effective amount of an active component derived from jojoba according to the invention, and in particular of a simmondsin as defined above or stereoisomeric forms, racemic mixtures, metabolites, esters or salts thereof, or mixtures thereof.

In accordance with the present invention, an active component according to the invention, and in particular a simmondsin as defined above or stereoisomeric forms, racemic mixtures, metabolites, esters or salts thereof, or mixtures thereof, may be administered orally, topically, parenterally, i.e. including subcutaneous injections, intravenous, intramuscular, intrasternal injection or infusion techniques, by inhalation spray, or rectally, in dosage unit formulations containing conventional non-toxic pharmaceutically acceptable carriers, adjuvants and vehicles. Oral administration is preferred. For example, oral administration may consist of an emulsion of refined jojoba flour as a so-called "milkshake".

In accordance with the method of the present invention, an active component according to the invention, and in particular a simmondsin as defined above or stereoisomeric forms, racemic mixtures, metabolites, esters or salts thereof, or mixtures thereof can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration, an active component according to the invention, and in particular a simmondsin as defined above or stereoisomeric forms, racemic mixtures, metabolites, esters or salts thereof, or mixtures thereof can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

For subcutaneous or intravenous administration, an active component according to the invention, and in particular a simmondsin as defined above or stereoisomeric forms, racemic mixtures, metabolites, esters or salts thereof, or mixtures thereof, if desired with the substances customary therefore such as solubilizers, emulsifiers or further auxiliaries, are brought into solution, suspension, or emulsion. Active components according to the invention, and in particular a simmondsin as defined above or stereoisomeric forms, racemic mixtures, metabolites, esters or salts thereof, or mixtures thereof can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The dose of an active component according to the invention, and in particular a simmondsin as defined above or stereoisomeric forms, racemic mixtures, metabolites, esters or salts thereof, or mixtures thereof, to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the infection and symptoms, and on the sex, age, weight, co-medication, and individual responsiveness of the human or animal to be treated and on whether the therapy is acute or prophylactic. The dose can be administered in the form of an individual dose, or divided into several, e.g. two, three, or four, individual daily doses.

The present invention further relates to a method for preparing an ester of a simmondsin as defined above comprising reacting simmondsin or said simmondsin with one or more suitable reagents according to techniques that are well known to a person skilled in the art, such as for instance described in Hosoda et al. (2000; Bioorganic & Med. Chem. etters 10:1439-1442).

The present invention will now be described with reference to clarifying examples that can by no means be limiting the protection of the invention and are given only with the purpose of enabling one skilled in the art, to perform the treatments. In the examples, all the percentages are given by weight, the temperature is the ambient temperature and the pressure is the atmospheric pressure unless otherwise indicated.

EXAMPLES

Example 1

Preparation of Refined, De-oiled Jojoba Flour

Jojoba seeds available on the market are fragmented and flaked in order to obtain jojoba flour containing oil and peel fragments. The peel fragments are removed through mechanical separation. The oil containing flour is treated by solvent extraction in order to eliminate the oil according to the procedure described in the U.S. Pat. No. 5,672,371, hence leading to refined, de-oiled jojoba flour.

Example 2

Preparation of a Polar Extract from Refined, De-oiled Jojoba Flour

The refined, de-oiled jojoba flour as obtained in example 1, is extracted by a polar solvent for example a ketone, notably acetone, methyl ethyl ketone, or a low boiling point alcohol, notably ethanol or methanol with a slight amount of water, usually less than 5 per cent by weight of water, to increase polarity of the solvent, during a period of time depending from the temperature of extraction and, if working at the reflux temperature, in a period of time from a few minutes to approx. 1 hour, which is sufficient to isolate the majority of the polar extract that contains the bioactive substances. Then, the polar extract is evaporated under vacuum to eliminate the solvent and the residue is further dried through lyophilization. The lyophilized product obtained, comprises primarily simmondsin and its derivatives naturally present in jojoba seeds. These compounds were submitted to biological trials as described in examples 4 and 5.

Example 3

Pharmaceutical Composition

This example illustrates a pharmaceutical composition comprising compounds isolated from the polar extract as prepared in example 2.

3.1: Isolation of Active Compounds

The polar extract as obtained in example 2 is further submitted to a series of liquid/liquid or solid/liquid extractions by means of solvents with varying solvency power (gradient or isocratic). 3 principal groups of molecules were isolated of the polar extract prepared in example 2, comprising:

- a group of 5 sugars: d-glucose, mannose, galactose, xylose and arabinose;
- a group of simmondsins: dimethylsimmondsin (major), desmethylsimmondsin and didesmethylsimmondsin;
- a group of simmondsin ferulates: ferulates (cis/trans) of dimethylsimmondsin, desmethylsimmondsin and didesmethylsimmondsin.

Individual compounds of the polar extract can be obtained through HPLC separation as shown in FIG. 1. A HPLC chromatogram of a total polar extract from a refined, de-oiled jojoba flour is represented. The numbers 1 to 7 indicate respectively: (1) 4,5 didesmethylsimmondsin (ça. 20%); (2) 5-desmethylsimmondsin (ça. 15%); (3) 4-desmethylsimmondsin (ça. 8%); (4) 4,5-dimethylsimmondsin (ça. 44%);

(5) ferulates (cis/trans) of 4-desmethyl-, 5-desmethyl & 4,5-didesmethylsimmondsin (ça. 7%); (6) ferulate of 4,5-dimethylsimmondsin (cis isomer) (ça 1.4%); (7) ferulate of 4,5-dimethylsimmondsin (trans isomer) (ça 4.3%).

According to the results of biological tests as described in examples 4 and 5 below, the compounds with highest biological activity, i.e. in particular an angiogenesis-inhibiting activity, were found in the group of simmondsins and/or the simmondsin ferulates (cis/trans). In these tests, the biological activity of the individual compounds was compared with the biological activity of a total polar extract containing all the above-mentioned compounds.

3.2: Preparation of a Pharmaceutical Composition

The biological active, angiogenesis-inhibiting compounds isolated from the refined, de-oiled jojoba flour may constitute a pharmaceutical composition alone, or can be admixed with a pharmaceutically acceptable exipient, adapted for the administration route of the pharmaceutical composition. This route can be without limitation an oral route, a topical route or a parenteral route (intravenous, intramuscular, subcutaneous . . . ).

The following examples 4 and 5 provide evidence for angiogenesis-inhibiting effects obtained with the different jojoba-derived compounds according to the invention. The compositions tested in these examples comprised:

a) refined, de-oiled jojoba flour
b) A1: a total polar extract of the jojoba flour
c) A2: simmondsin derivatives (partially purified, contains mainly dimethylsimmondsin, desmethylsimmondsin (2 isomers) and didesmethylsimmondsin, all in the hydroxyl form)
d) A3: simmondsin ferulates (mixture of ferulates of all in A2 described simmondsins in the hydroxyl form, +/−65% substantially pure)
e) A4: 4,5-dimethylsimmondsin (substantially pure, in the hydroxyl form)
f) A5: 4,5-dimethylsimmondsin ferulate (cis/trans) (substantially pure, in the hydroxyl form)
g) B3: 4-desmethylsimmondsin (substantially pure, in the hydroxylform)
h) B4: 5-desmethylsimmondsin (substantially pure, in the hydroxylform)
i) B5: 4,5-didesmethylsimmondsin (substantially pure, in the hydroxylform)
j) B6: partially purified simmondsin ferulates (mixture of all in A3 described simmondsin ferulates in the hydroxyl-form, +/−87% substantially pure)

Example 4

Biological Tests

In this example biological trials have been performed as explained below by applying chorion allantois membrane (CAM) assays. CAM assays are based on Nguyen et al. (1994, Microvasc. Res. 47 (1):3140). Fertilized chicken eggs are incubated during 4 days at 37° C. Subsequently, the egg shell is opened to disclose the CAM. In order to reduce the pressure on the CAM for improving its manipulating properties, 2 to 3 ml albumen is removed. The opening is closed using cellophane tape and the eggs are further incubated until day 9 for application of the liquid test compounds using different concentrations. Dulbecco's modified Eagle medium (DMEM) was used as a negative control, whereas Vascular Endothelial Growth factor (VEGF) was used as a positive control (stimulator of angiogenesis). A total polar extract from refined, de-oiled jojoba flour, dimethylsimmondsin purified from this extract and a commercially known angiogenesis inhibitor (Tangeritin) were compared in their angiogenesis-inhibiting activity towards VEGF stimulated angiogenesis in the CAM's. Each of these solubilized test compositions was pipetted on a sterile plastic disc (10 mm diameter) and dried under sterile conditions.

Figure 2A:
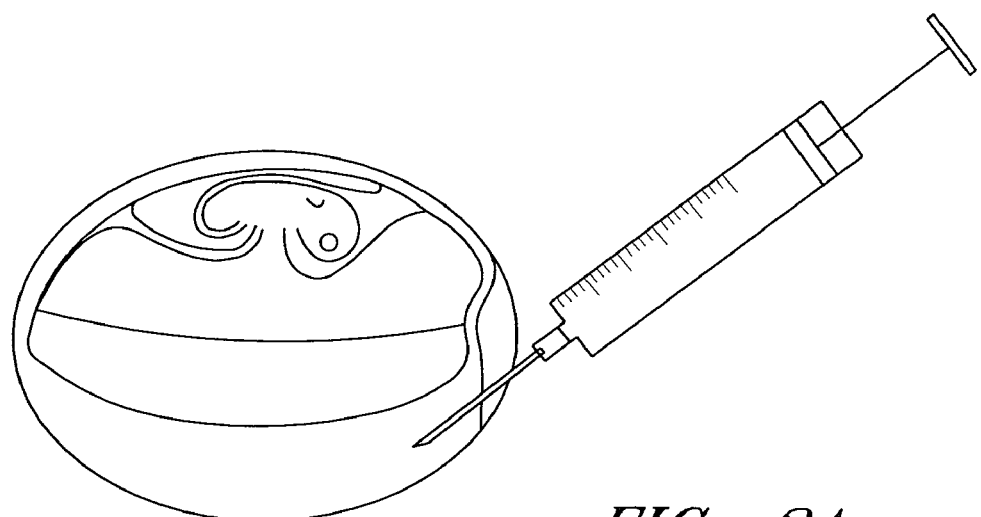
FIG. 2 illustrates the concept of a chorioallantoic membrane (CAM) assay.
Figure 2B:
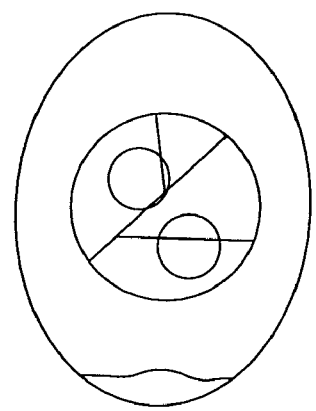
Figure 2C:
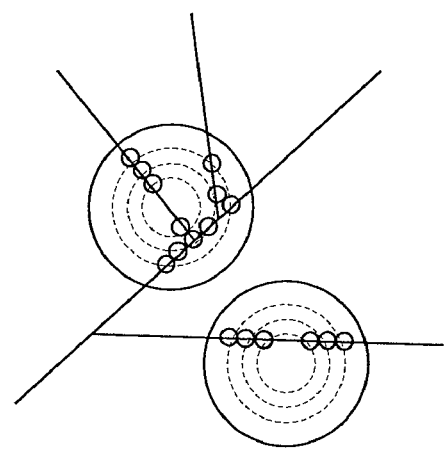

Each disc was treated with cortisone acetate (100 µg/50 µl) in order to avoid inflammatory reactions. After drying, the discs were placed on the CAM with the charged side facing the CAM. The control disc (DMEM) was placed at 1 cm of the disc containing the test component. The opening was sealed with cellophane tape and the eggs were further incubated. At day 11, the tape and discs were removed and 10% buffered formaline was sprayed over the CAM. Eggs were allowed to dry for 2 to 4 h at room T°. Then, the CAM was cut out of the egg and mounted on a glass slide. The vascular density index is measured according to Harris-Hooker et al. (1983; J. Cell. Physiol. 114:302-310); all micro vessels that cross 3 concentric circles with a diameter of 6, 8 and 10 mm were counted, as illustrated on FIG. 2. On FIG. 2A, the situation on day 4 is illustrated: albumen is removed to drop the CAM pressure. On FIG. 2B the situation on day 9 is illustrated: discs unloaded or loaded with test compound are implanted. FIG. 2C illustrates the situation on day 11: the intersections between vessels and 3 concentric circles are counted and the angiogenetic index is calculated.

The angiogenetic Index (AI) is expressed as {(t/c)×100}−100, whereby t=total number of crossing vessels where the disc containing the test component was located, and c=total number of crossing vessels where the control disc was located. The test composition is classified positively when AI>10% and negatively when AI<10%. When AI ranges between −10% and +10%, no effect is attributed to the examined test composition.

4.1: Experiment 1

Figure 3:
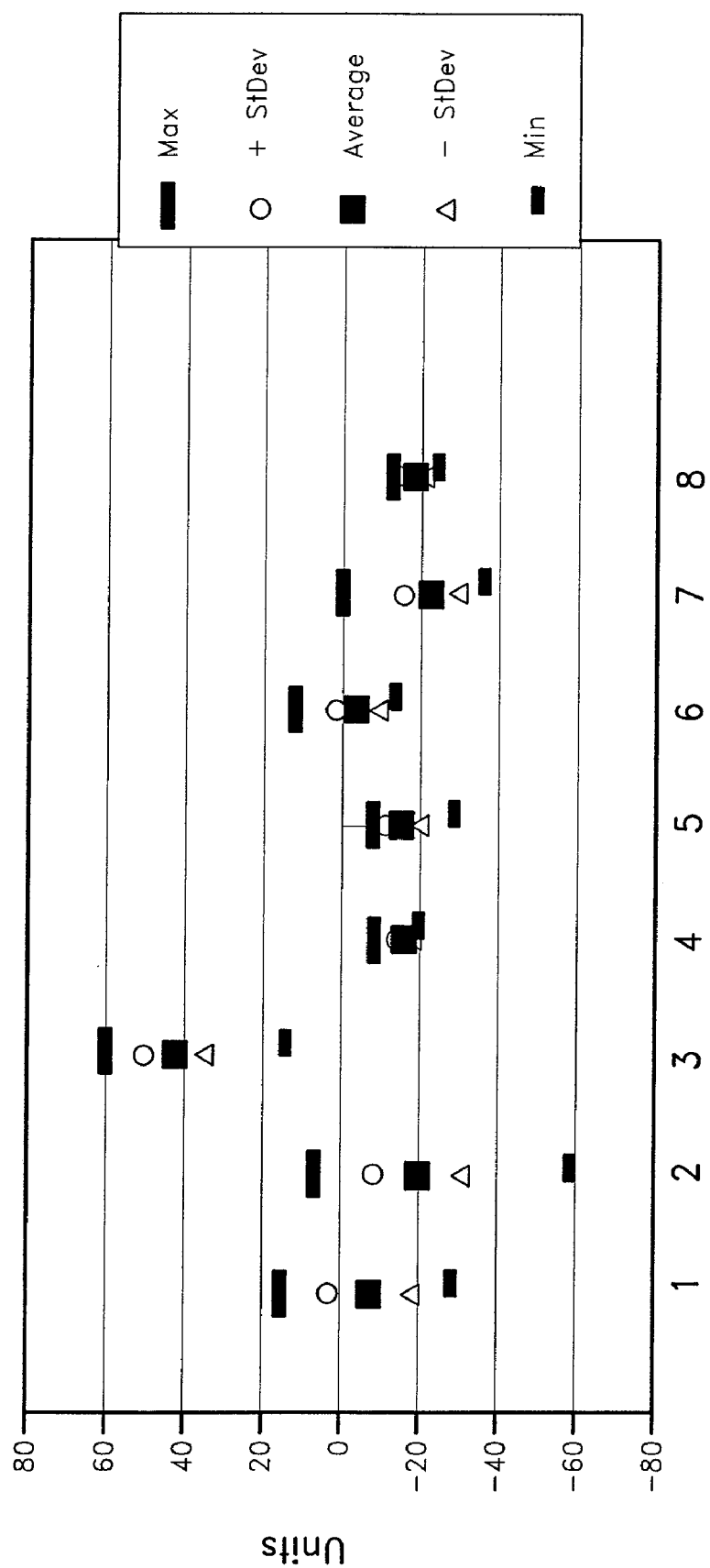
FIGS. 3, 4 and 5 illustrate results of three different CAM assays using different simmondsin compounds according to the invention.

Results of a first experiment are shown in FIG. 3 and in table 3. In the FIG. 3 and table 3 (1) refers to DMSO, (2) to DMEM, (3) to VEGF, (4) to the polar extract, (5) to the total polar extract+VEGF; (6) to dimethylsimmondsin; (7) to dimethylsimmondsin+VEGF and (8) to tangeritin.

TABLE 3

| | Test Substance | | | | | | | |
|---|---|---|---|---|---|---|---|---|
| | 1 | 2 | 3 | 4 | 5 | 6 | 7 | 8 |
| Max | 16.130 | 7.920 | 61.040 | −7.920 | −7.460 | 12.840 | 0.080 | −12.260 |
| Average | −6.998 | −19.043 | 43.060 | −15.500 | −15.034 | −3.322 | −22.220 | −17.848 |
| Min | −27.970 | −59.400 | 15.120 | −18.640 | −27.630 | −12.660 | −35.800 | −23.880 |
| St Dev | 20.719 | 22.573 | 15.151 | 4.334 | 8.104 | 10.369 | 13.467 | 4.236 |
| St Error | 9.266 | 9.215 | 5.726 | 1.938 | 3.624 | 4.637 | 5.498 | 1.894 |
| # samples | 5 | 6 | 7 | 5 | 5 | 5 | 6 | 5 |

Results showed that the VEGF stimulated CAM showed significant blood vessel growth compared with the negative control group (DMEM). Total polar extract (A1) as well as substantially pure dimethylsimmondsin (A4) showed significant angiogenesis inhibition comparable with tangeritin. The addition of jojoba compounds combined with VEGF, cancelled the effect of VEGF completely, which suggests a real angiogenesis-inhibiting effect.

4.2: Experiment 2 and 3

Figure 4:
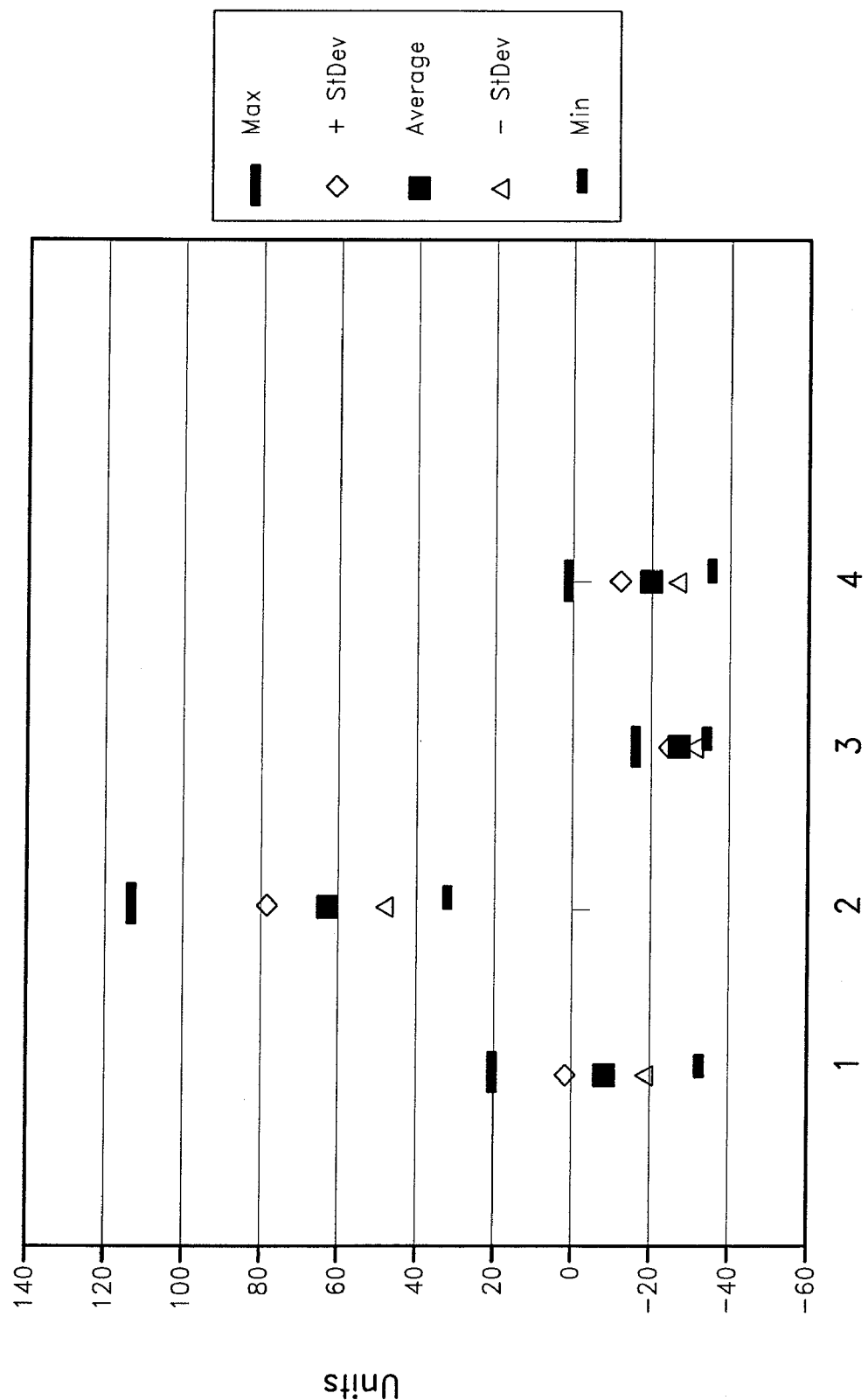
Figure 5:
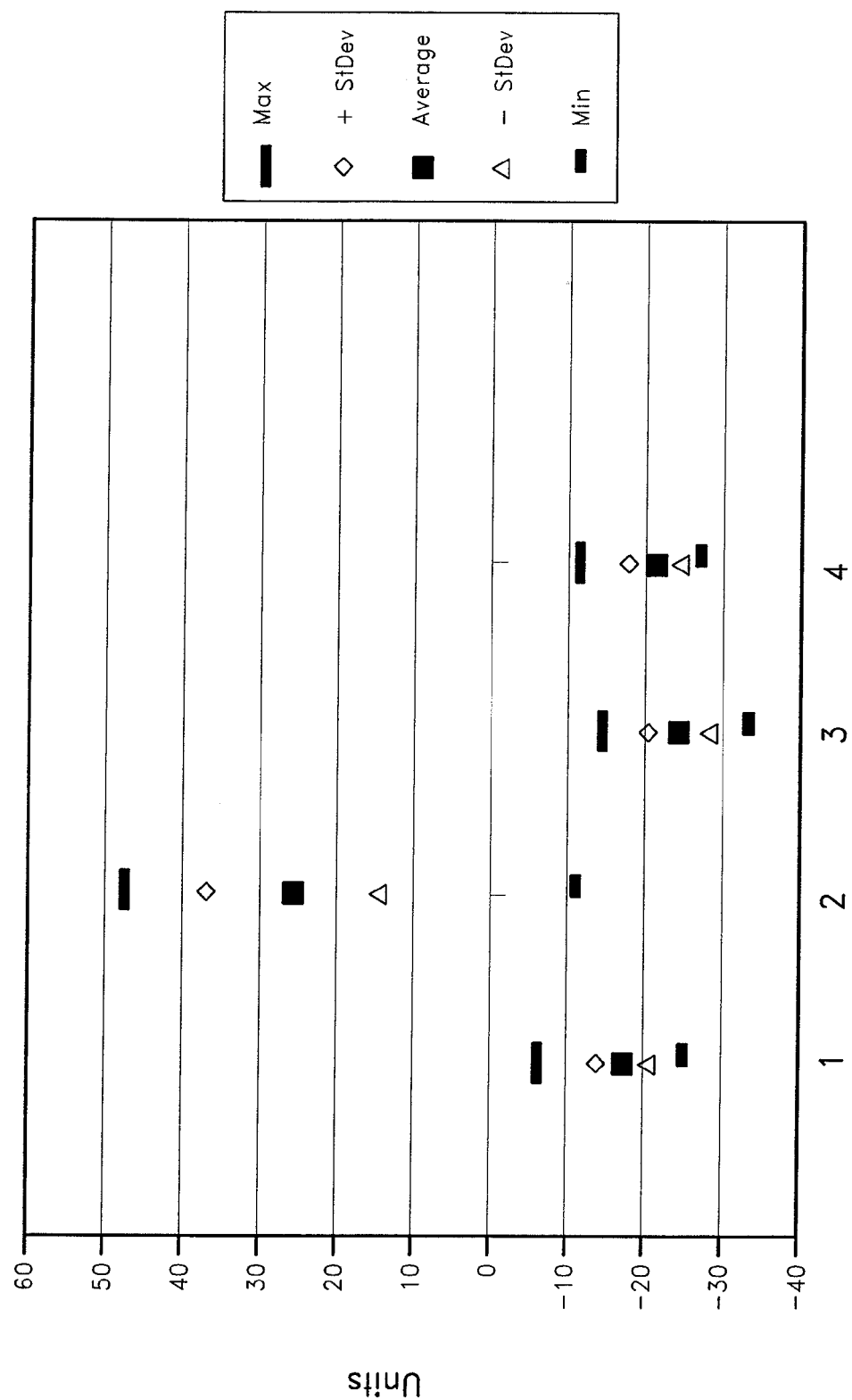

Results of a second and a third experiment are shown in FIG. 4 and in table 4 and in FIG. 5 and table 5, respectively. In FIG. 4 and table 4, (1) refers to DMEM, (2) to VEGF; (3) to the polar extract and (4) to dimethylsimmondsin. In FIG. 5 and table 5 (1) refers to DMEM, (2) to VEGF; (3) to the polar extract+VEGF and (4) to dimethylsimmondsin+VEGF.

TABLE 4

| | Test Substance | | | |
|---|---|---|---|---|
| | 1 | 2 | 3 | 4 |
| Max | −16.700 | 112.700 | 20.000 | 1.110 |
| Average | −28.180 | 62.890 | −8.860 | −19.670 |
| Min | −35.000 | 31.800 | −33.300 | −35.700 |
| St Dev | 6.936 | 30.524 | 19.587 | 15.090 |
| St Error | 13.651 | 13.651 | 8.760 | 6.749 |
| # samples | 5 | 5 | 5 | 5 |

TABLE 5

| | Test Substance | | | |
|---|---|---|---|---|
| | 1 | 2 | 3 | 4 |
| Max | −6.560 | 47.470 | −14.560 | −11.720 |
| Average | −17.372 | 25.586 | −24.395 | −21.248 |
| Min | −25.000 | −11.270 | −33.330 | −27.180 |
| St Dev | 6.710 | 22.437 | 7.702 | 6.535 |
| St Error | 3.001 | 10.034 | 3.144 | 2.668 |
| # samples | 5 | 5 | 6 | 6 |

Results of a second and third experiment confirmed the angiogenesis-inhibiting activity of the total polar extract (A1) and the dimethylsimmondsin derived thereof. Although substantially pure dimethylsimmondsin (A4) was used in the same concentration as the total polar extract, its angiogenesis-inhibiting properties were lower than the total polar extract but nevertheless still significant. This suggests that in this example other compounds present in the total polar extract different from dimethylsimmondsin (A4) are more potent angiogenesis-inhibiting agents.

Example 5

Biological Tests

The following example illustrates angiogenesis-inhibiting effects of a polar extract of refined, de-oiled jojoba flour and simmondsin or derivatives thereof, comprised in the extract.

Human Vascular Endothelial Cell (HUVEC) isolations were obtained as described by Jaffe et al (J. Clin. Invest. 1973; 52:2745-2746), and cultured to confluence on fibronectin-coated dishes in M199 supplemented with 20 mM HEPES (pH 7.3), 10% human serum, 10% heat-inactivated new born calve serum (NBCS), 150 µg/ml crude endothelial cell growth factor (ECGF), 2 mM L-glutamine, 5 U/ml heparin, 100 IU/ml penicillin and 100 µg/ml streptomycin at 37° C. under 5% $CO_2$/95% air atmosphere. The confluent HUVEC cultures (passage 0) were detached by trypsin/EDTA treatment, pooled and cultured after a split ratio of 1:3 till confluence (passage 1). Then the pooled HUVEC were frozen in 10 cm² aliquots in vials in liquid nitrogen. One week before the proliferation, vials of HUVEC (passage 1) were thawed and cultured (after a split ratio of 1:3) to confluence (passage 2).

5.1: Cell Proliferation Measured by ³H-thymidine Incorporation

In this first experiment, confluent cultures of HUVEC (passage 2) were detached by trypsin/EDTA solution, and allowed to adhere and spread at an appropriate cell density on gelatin-coated dishes in M199-HEPES medium supplemented with 10% heat-inactivated NBCS and 100 IU/ml penicillin and 100 µg/ml streptomycin. After 18 h the HUVEC were stimulated with 6.25 ng/ml vascular endothelial growth factor type A (VEGF-α) in M199-HEPES, 100 IU/ml penicillin and 100 µg/ml streptomycin, 10% NBCS in duplicate wells, with or without the indicated simmondsin derivatives. After an incubation period of 48 h, a tracer amount (0.5 µCi/well) of [³H]-thymidine was added and the cells are incubated for another 6 h period. Subsequently, the cells were washed with PBS, [³H]-labelled DNA was fixed with methanol, and precipitated in 5% trichloroacetic-acid, and finally dissolved in 0.5 ml 0.3 M NaOH and counted in a liquid scintillation counter.

Figure 6:
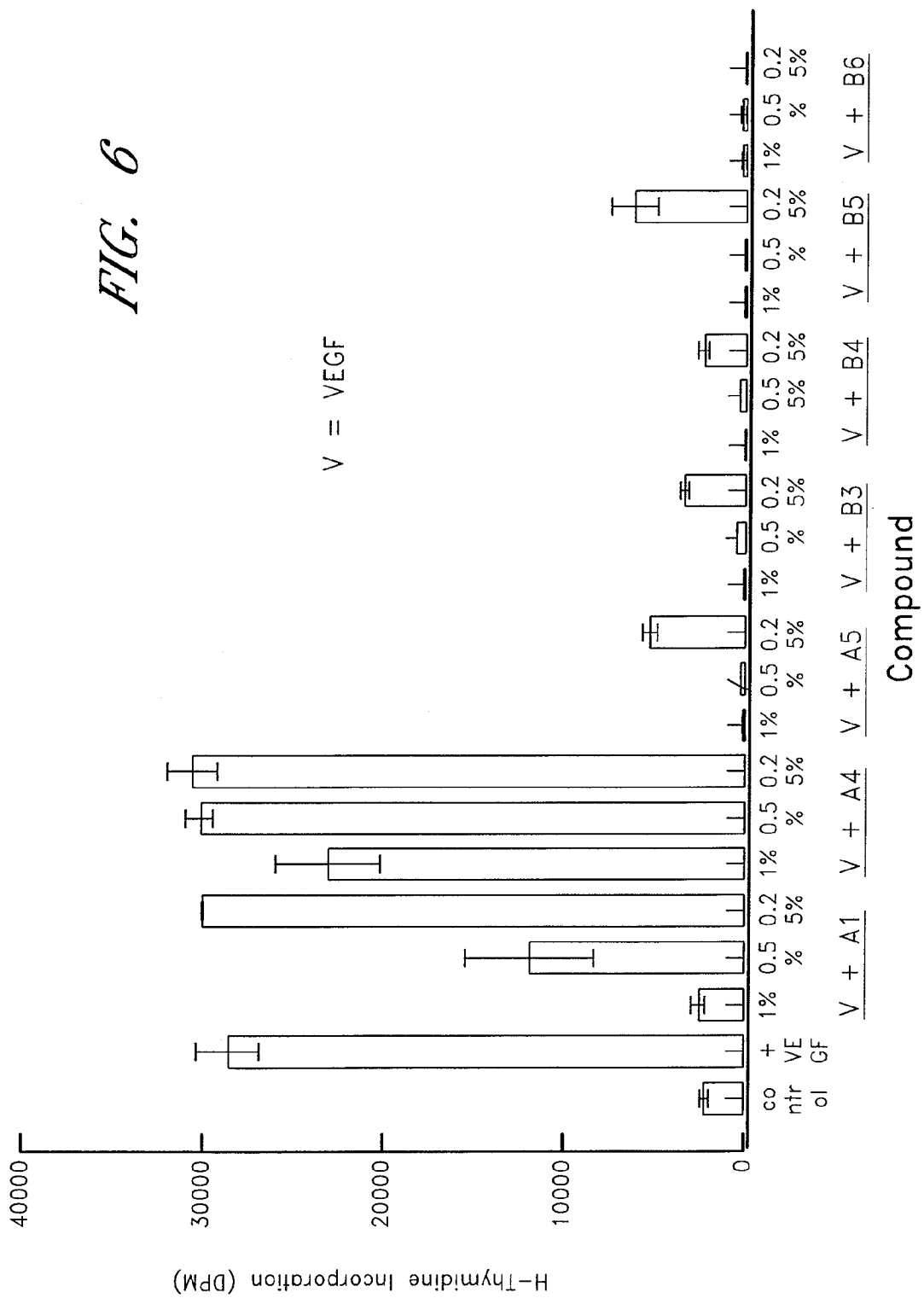
FIG. 6 illustrates the inhibition of VEGF-α-induced HUVEC proliferation by simmondsins.

FIG. 6 illustrates inhibition of VEGF-α-induced HUVEC proliferation by simmondsin derivatives. Non-confluent HUVEC were cultured for 48 h in the absence or presence of VEGF-α, or VEGF-α in combination with the indicated simmondsin derivatives A1, A4, A5, B3 B4, B5, B6 (in w/v) in M199 supplemented with 10% NBCS. After 48 h, a tracer amount of [³H]thymidine was added to the medium and the incubation continued in the same medium for another 6 h and [³H]thymidine incorporation was determined. The data are expressed as mean±SEM of triplicate wells.

The present experiment provides evidence for the anti-angiogenic effect of simmondsin derivatives. Simmondsin derivatives are able to inhibit VEGF-induced human endothelial cell proliferation. According to FIG. 1; the dimethylsimmondsin (A4) is a major constituent of the total polar extract (A1). FIG. 6 clearly demonstrates in this example that the biological activity of the used polar extract is mainly due to the presence of the substances other than dimethylsimmondsin.

5.2: Cell Proliferation Measured by Cell Counting.

A confluent monolayer of HUVEC (passage 2) was detached by trypsin/EDTA solution, and allowed to adhere and spread at cell density of 15% confluency in gelatine-coated flasks in M199-HEPES medium supplemented with 10% heat-inactivated NBCS and 100 IU/ml penicillin and 100 µg/ml streptomycin. After 18 h the HUVEC were stimulated with 2.5 ng/ml basic fibroblast growth factor (βFGF) in M199-HEPES, penicillin/streptomycin, 10% NBCS and 0.1% DMSO in triplicate wells for 6 days, with an refreshment of the medium (+compositions) at day 4, with compositions A1, A2, A3, A4, or A5 or vehicle (=0.1% DMSO). The morphology of the cells was microscopically evaluated and the cell number was determined by image analysis.

Figure 7:
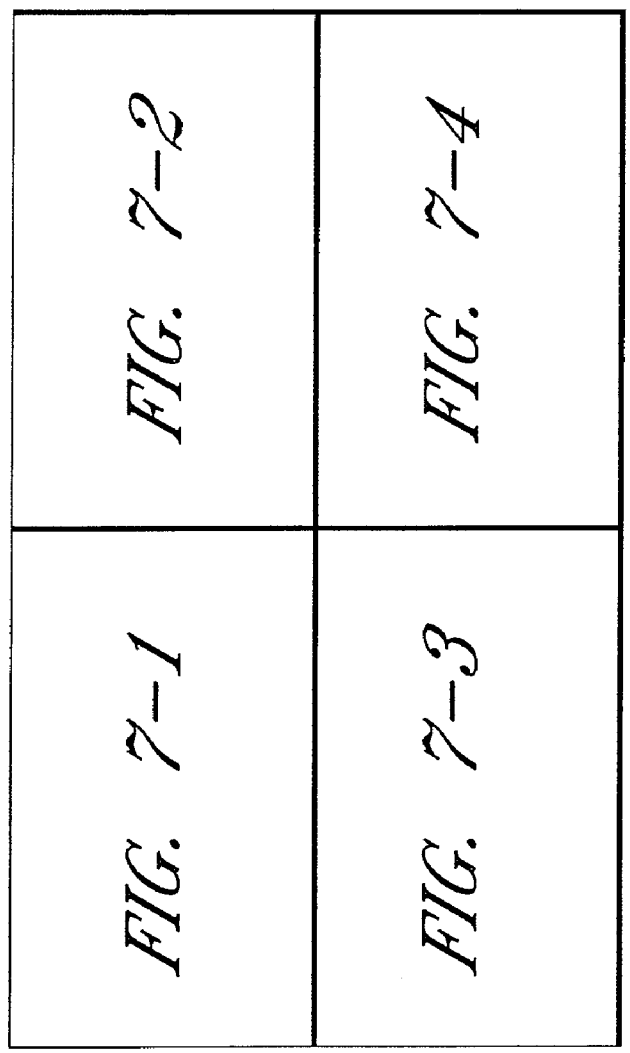
FIG. 7 shows the effect of simmondsins on 15% and 100% confluent monolayers of HUVEC stimulated with βFGF.
Figures 1, 7:
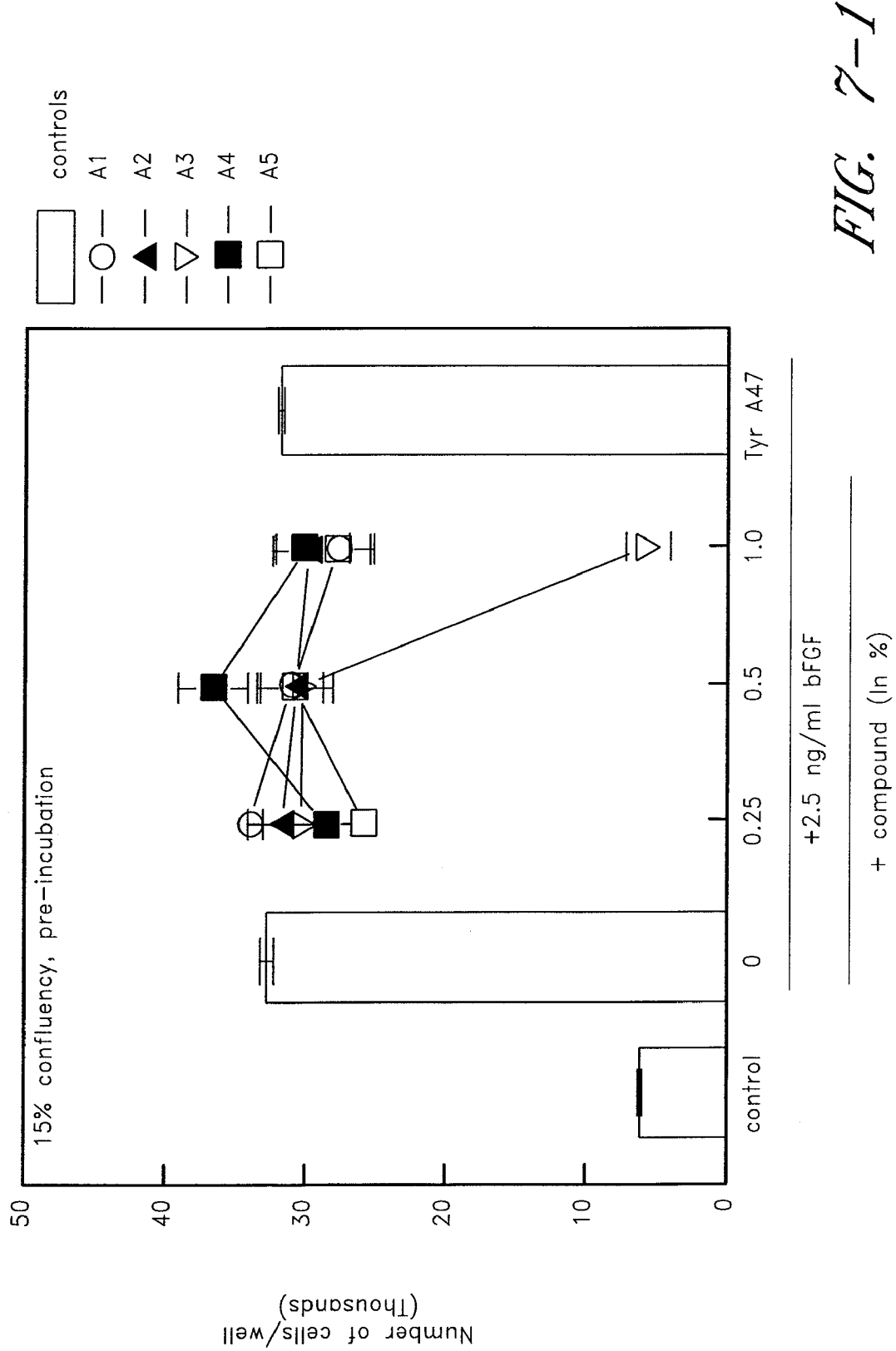
Figures 2, 7:
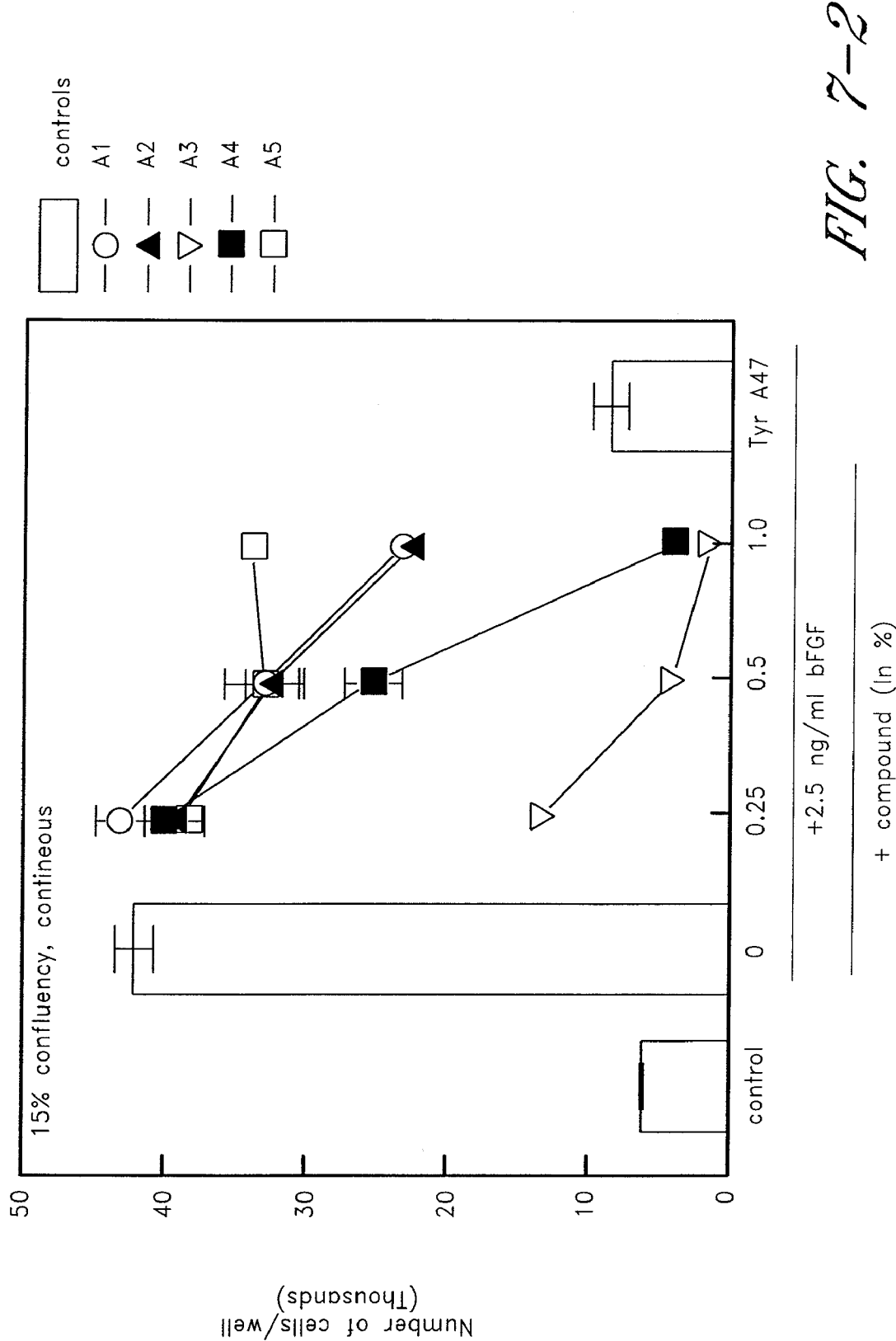
Figures 3, 7:
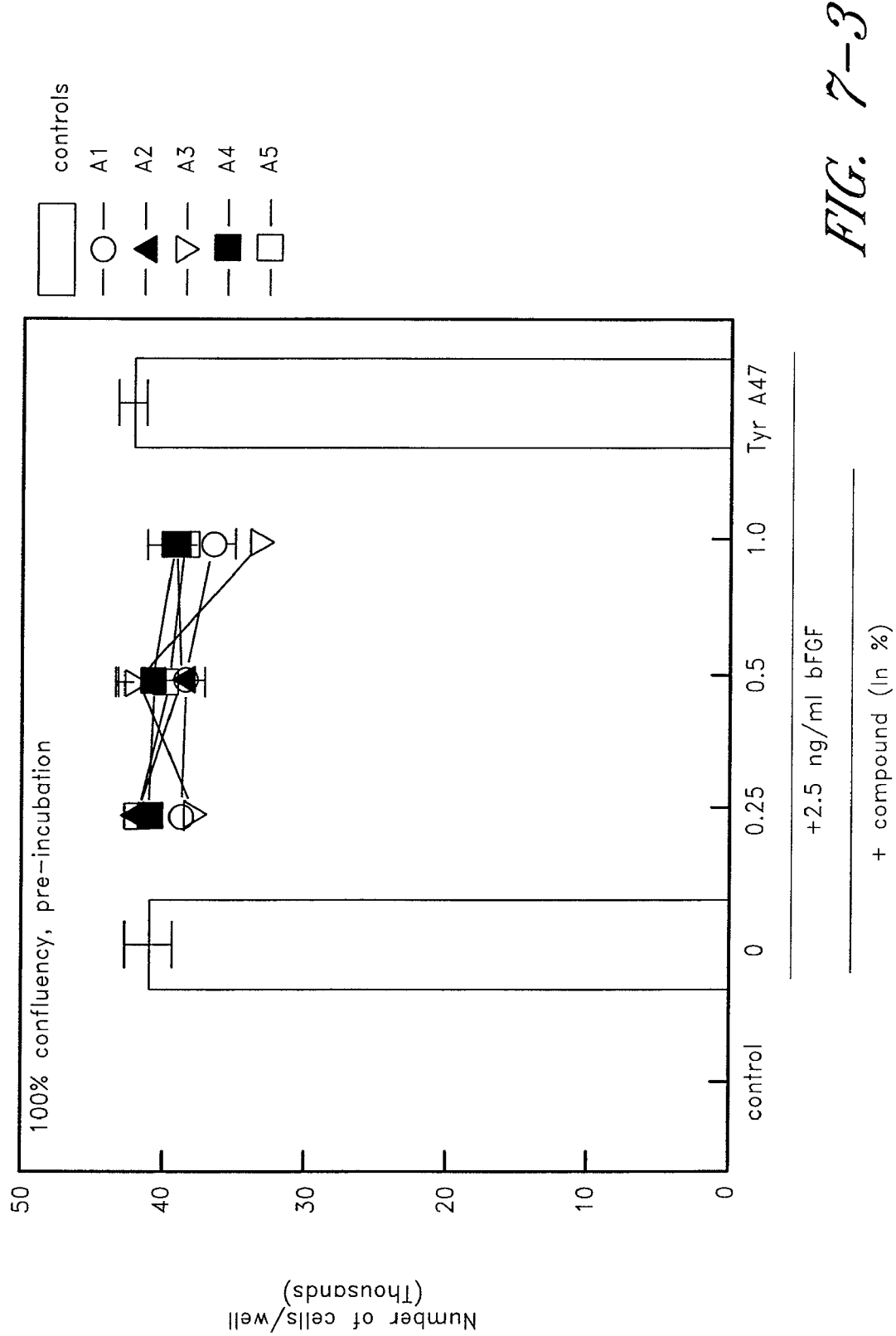
Figures 4, 7:
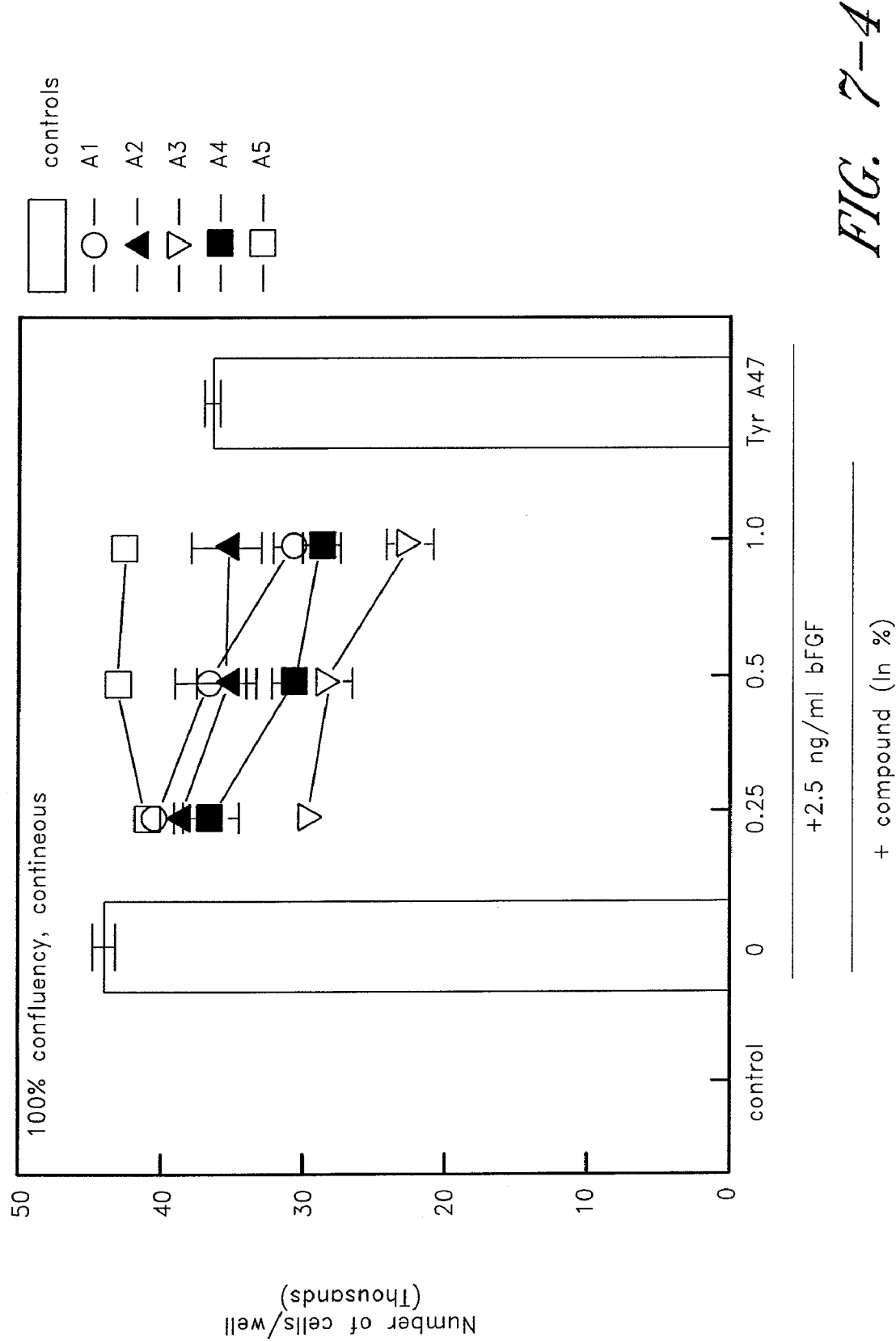

FIG. 7 illustrates the effect of above-indicated simmondsin derivatives on 15% and 100% confluent monolayers of HUVEC stimulated with βFGF. Non-confluent (15%) and confluent (100%) monolayers of HUVEC were pre-incubated (left panels) or continuously incubated (right panels) with or without the indicated concentrations (w/v) of compositions A1, A2, A3, A4, A5 in the continuous presence of βFGF. After 3 (100%) or 6 days (15%) pictures were taken and the number of cells/cm² was determined and expressed as mean±std (as indicated by error bars) of triplicate wells.

The present experiment provides evidence for the anti-angiogenic effect of simmondsin derivatives. The tested compositions were able to inhibit βFGF-induced human endothelial cell proliferation. Since 100% confluent cells continuously treated with the above-indicated compositions show no significant mortality, it can also be concluded that the above-indicated compositions are not cytotoxic. Results of this experiments showed that the above-cited compositions are not significantly cytoxic for an organism, but show an important inhibition on proliferating endothelial cells.

5.3: In vitro Angiogenesis Assay: Tube Formation in 3-D Fibrin Matrices

Human fibrin matrices were prepared by the addition of 0.1 U/ml thrombin to a commercially obtained (Chromogenix AB, Mölndal, Sweden) mixture of 2 mg/ml fibrinogen (final concentrations), 2 mg/ml Na-citrate, 0.8 mg/ml NaCl, 3 µg/ml plasminogen in M199 medium and 2.5 U/ml factor XIII. 100 µl aliquots of this mixture were added to the wells of 96-well plates. After clotting at room temperature, the fibrin matrices were soaked with M199 supplemented with 10% HS and 10% NBCS for 2 h at 37° C. to inactivate the thrombin. Frozen human microvascular endothelial cells (hMVEC, 0.7×10⁵ cells/cm²) were thawed and seeded in a 1.8:1 split ratio on the fibrin matrices and cultured for 24 h in M199 medium supplemented with 10% human serum, 10% NBCS, and 100 IU/ml penicillin and 100 µg/ml streptomycin. Then, the hMVEC were stimulated with the mediators and/or simmondsin derivatives for 7 days. Fresh medium, containing the mediators and/or inhibitors, were added every second day. Invading cells and the formation of tubular structures of hMVEC in the three-dimensional fibrin matrix were analysed by phase contrast microscopy. The total length of tube-like structures of four microscopic fields (7.3 mm²/field) were (clockwise) measured using an Olympus CK2 microscope equipped with a monochrome CCD camera (MX5) connected to a computer with Optimas image analysis software, and expressed as mm/cm² (Koolwijk et al. J. Cell Biol. 1996, 132:1177-188).

Figure 8A:
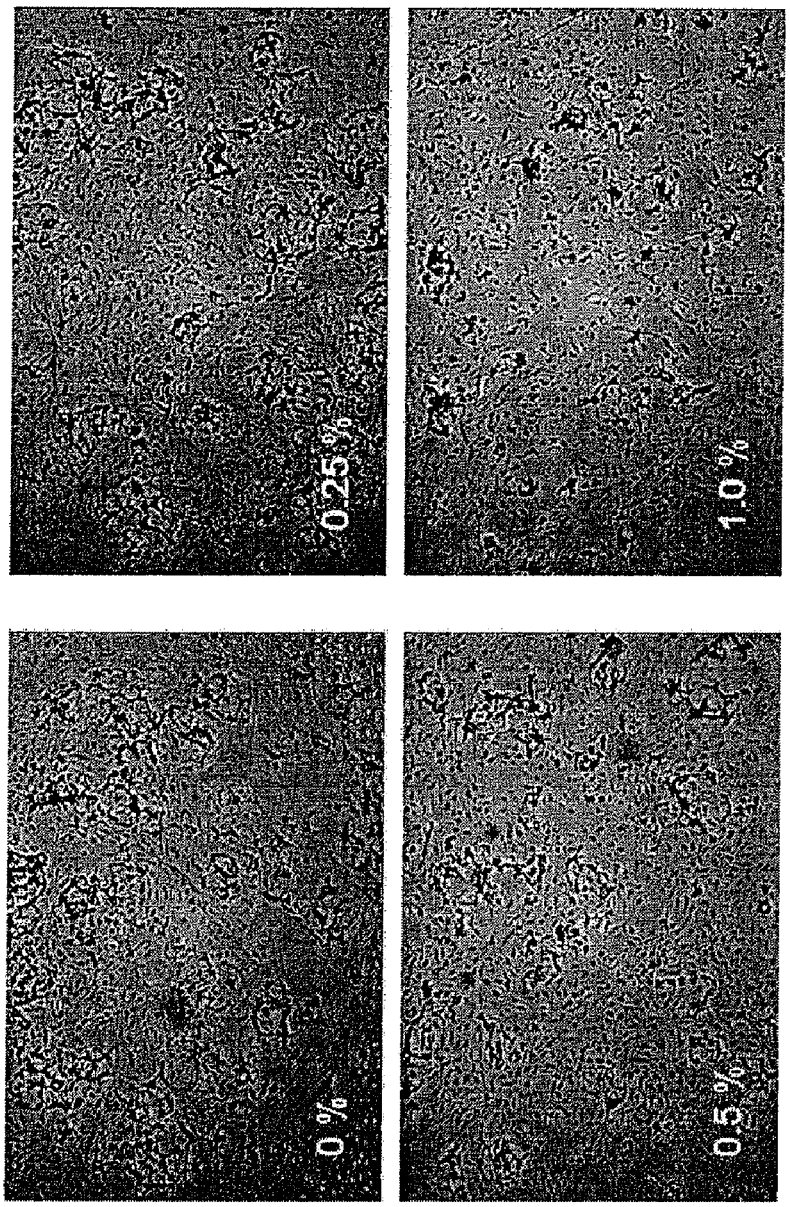
FIG. 8 shows the effect of simmondsins on in vitro tube formation in 3-D fibrin matrices by hMVEC.
Figure 8B:
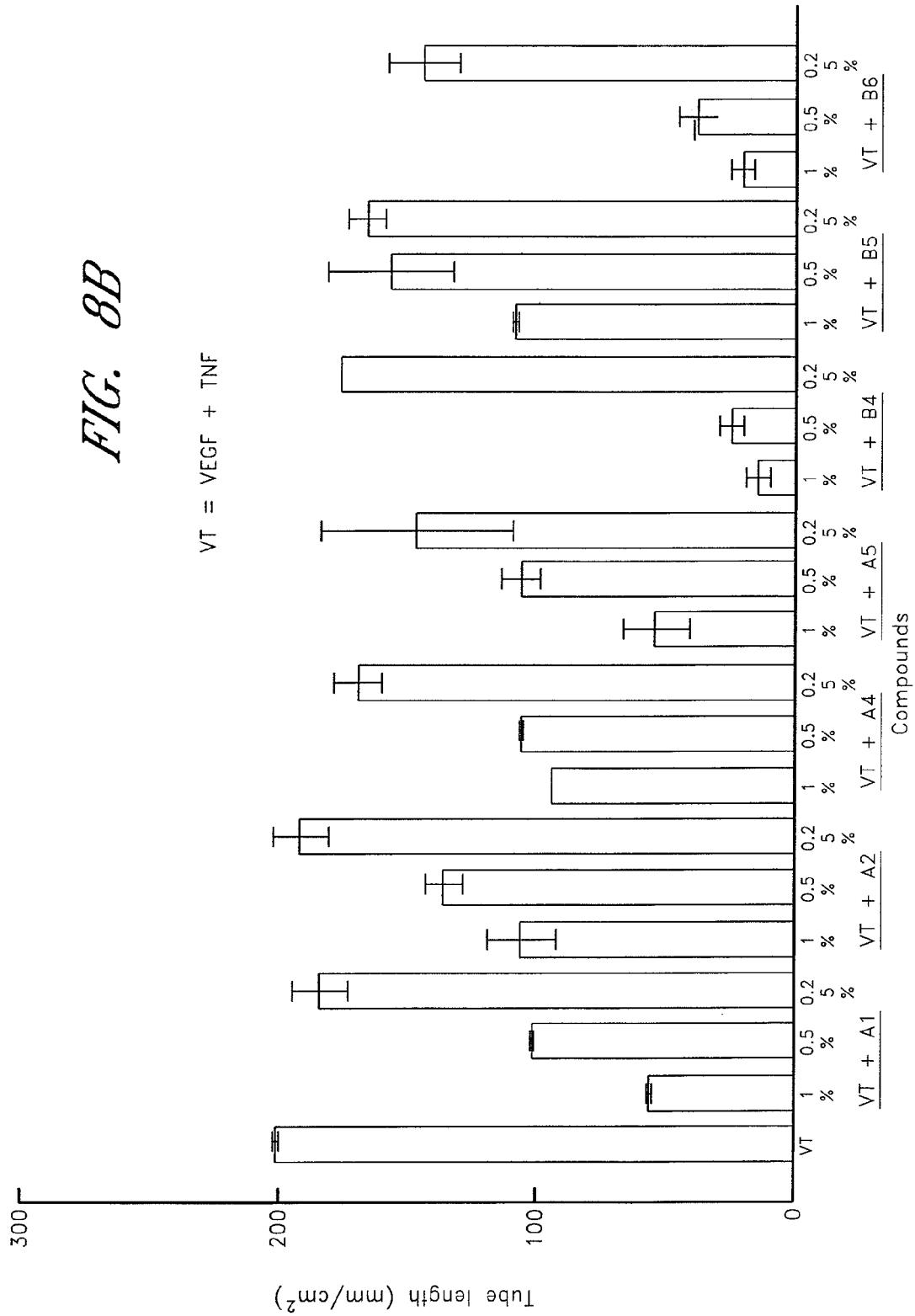

FIG. 8 shows the effect of simmondsin derivatives on in vitro tube formation in 3-D fibrin matrices by hMVEC. HMVEC were cultured on top of a 3-D fibrin matrix in M199, 10% human serum, 10% NBCS supplemented with VEGF-A (25 ng/mL) and TNFα (10 ng/mL) in the presence or absence of the indicated concentrations (w/v) of the compositions A1, A2, A3, A4, A5, B4, B5 and B6. After 7 days of culture microscopic pictures (FIG. 8 A-Effect of composition A1) were taken and the total tube length (mm/cm²) was measured using image analysis equipment. The data are expressed as the mean of two wells indicated by the error bars (FIG. 8 B).

The results of this experiment show that simmondsin derivatives are able to inhibit VEGF-induced in vitro tube formation by human microvascular endothelial cells in 3-dimensional fibrin matrices. The highest biological activity was seen with desmethylsimmondsin, didesmethylsimmondsin and their respective ferulates.

5.4 Ex vivo Angiogenesis Assay

An ex vivo angiogenesis assay was performed as described previously (Deckers et al, Lab. Invest. 2001. 81:5-15). Seventeen-day-old foetuses were removed from pregnant Swiss albino mice and metatarsals were dissected. The isolated metatarsals were cultured in 24-well plates in 150 µl minimal essential medium (αMEM; Life Technologies, Breda, The Netherlands) supplemented with 10% (v/v) heat-inactivated fetal bovine serum and 100 IU/ml penicillin and 100 µg/ml streptomycin (Life Technologies) for 72 hours. Cultures were performed in sextuple and each experiment was repeated at least twice. After 72 hours (adhesion phase), the metatarsals were attached to the culture plastic and medium was replaced by 250 µl fresh medium+10 ng/ml rhVEGF-A (Reliatech, Braunschweig, Germany) in the presence or absence of 1% (w/v) composition A1. The MMP inhibitor marimastat was kindly provided by Chiroscience Inc. (Cambridge, United Kingdom). Metatarsals were cultured for 14 days and medium was replaced every 7 days. At the end of the culture period, cultures were fixed in ZnMF fixative for 15 minutes at room temperature and subsequently stained for PECAM-1.

Figure 9A:
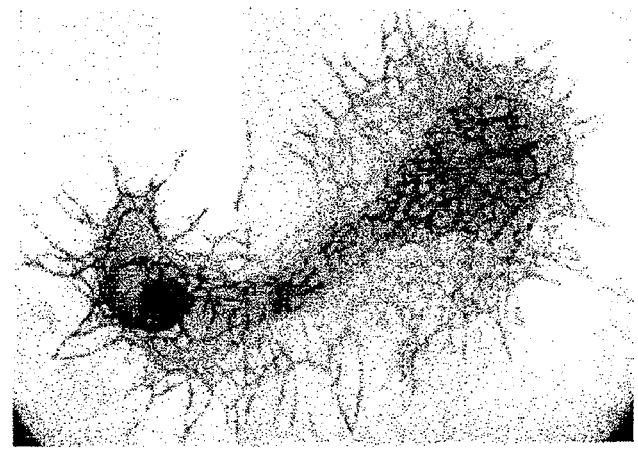
FIG. 9 illustrates the effect of a total polar extract of jojoba flour on VEGF-induced ex vivo tube formation from foetal mouse metacarpals.
Figure 9B:
Figure 9C:
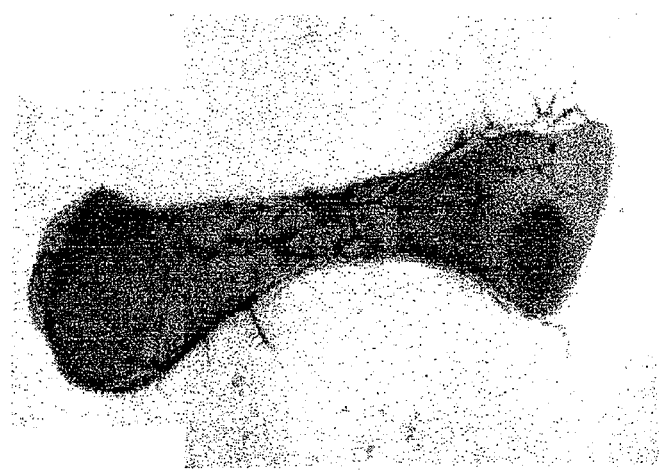

FIG. 9 illustrates the effect of composition A1 on VEGF-induced ex vivo tube formation from foetal mouse metacarpals. The figures illustrate gross appearance of PECAM-1 positive tube-like structures. Foetal mouse metacarpals incubated with 10 ng/ml VEGF in the absence (FIG. 9A) or presence of 10 µM marimastat (FIG. 9B) or 1% (w/v) of composition A1 (FIG. 9C). After 14 days of culture, the tube-like structures were stained for PECAM-1.

Results of this experiment showed that control bones exhibited a clear growth of blood vessels (FIG. 9A). The above-cited compositions clearly inhibited the growth of blood vessels. The bones treated with the above-cited compositions remained viable. In this experiment 1% of a total polar extract (A1) (FIG. 9C) was more effective in inhibiting angiogenesis than marimastat, a commercially matrix metalloproteinase with angiogenesis-inhibiting properties (FIG. 9B).

In conclusion, the present example provides evidence that the tested compositions inhibit the ex-vivo outgrowth of tube-like structures of endothelial cells from foetal mouse metacarpals. The tested compositions showed an angiogenesis-inhibiting activity but were not toxic to bone cells.

5.5: In vivo Angiogenesis: Matrigel-chamber Assay

The in vivo matrigel chamber assay was performed as described by Kragh et al (Int. J. Oncol. 2003 22:305-311). Briefly, plexiglas ring/nylon net filter-chambers (0.2 ml) containing growth factor-reduced Matrigel and 200 ng basic fibroblast growth factor (β-FGF) were subcutaneously implanted into the flanks of 3-months old FVB/N mice. Mice were fed with or without refined, de-oiled jojoba flour (2.7% w/w) containing all simmondsins and its natural occurring derivates, mixed in Crispy Rat food. Chamber angiogenesis was scored superficial on day 14 post-implantation.

Figure 10:
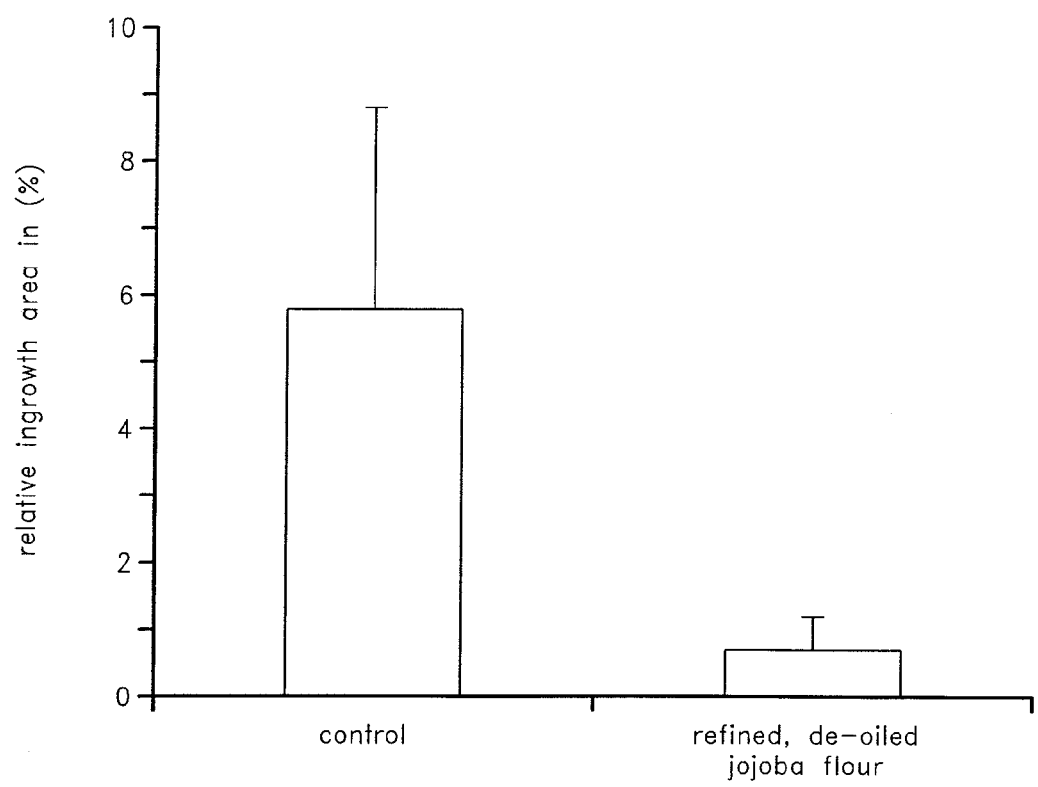
FIG. 10 illustrates the effect of refined, de-oiled jojoba flour on βFGF-induced vascularisation of matrigel chambers in vivo.

FIG. 10 illustrates the effect of refined, de-oiled jojoba flour (2.7%) on βFGF-induced vascularisation of matrigel chambers in vivo. The relative ingrowth area is expressed as mean±range (as indicated by error bars) of two chambers as % of total matrigel area. This experiment shows that tested simmondsins inhibit in vivo neovascularization of matrigel chambers in mice after oral treatment.

In conclusion, anti-angiogenic effects of simmondsin derivatives have been illustrated. The above-indicated simmondsin derivatives are able to i) inhibit VEGF- and βFGF-induced human endothelial cells proliferation (see 5.1 and 5.2) ii) inhibit VEGF-induced in vitro tube formation by human microvascular endothelial cells in 3-dimensional fibrin matrices (see 5.3), iii) inhibit the ex vivo outgrowth of tube-like structures of endothelial cells from fetal mouse metacarpals (see 5.4), and iv) inhibit in vivo neovascularization of matrigel chambers in mice (see 5.5).

In addition, from the results of these biological experiments it can be concluded that
a) desmethyl- and didesmethylsimmondsins and their respective ferulates show high angiogenesis-inhibiting properties as shown by both in vitro and in vivo assays.
b) dimethylsimmondsin ferulate shows a higher angiogenesis-inhibiting activity than the unsubstituted dimethylsimmondsin Furthermore, it was demonstrated that different compounds according to this invention show quantitative and qualitative differences on various steps involved in the angiogenetic process.

Example 6

Oestrogenic Bioassay

The present example provides evidence that active components according to the invention do not have a significant oestrogen-like activity.

In an experiment, yeast cells (*Saccharomyces cerevisiae*) containing a human oestrogen receptor (100 μl) was added to 25 ml growth medium. The growth medium comprised
D-glucose (2.5 ml from 20 g D-glucose in 80 ml water);
L-aspartic acid (0.625 ml from 400 mg in 100 ml water);
vitamin solution (0.250 ml from 8 mg thiamine, 8 mg pyridoxine, 8 mg panthotenic acid, 40 mg inositol and 20 ml biotin solution (2 mg in 100 ml water) in 180 ml water);
L-threonine (0.2 ml from 2.4 g in 100 ml water), copper (II)sulphate (0.0625 ml from 160 mg in 50 ml water);
minimal medium (22.5 ml from 1 l water composed of 13.61 g potassium dihydrogenphosphate, 1.98 g ammonium sulphate, 4.2 g potassium hydroxide, 1 ml iron (III)sulphate (40 mg in 50 ml water), 50 mg L-leucine, 50 mg L-histidine, 50 mg adenine, 20 mg L-arginine hydrochloride, 20 mg L-methionine, 30 mg L-tyrosine, 30 mg L-isoleucine, 30 mg L-lysine hydrochloride, 25 mg L-phenylalanine, 100 mg L-glutamic acid, 150 mg L-valine, 375 mg L-serine); and chlorophenol red beta-D-galactopyranoside (0.250 ml).

17 beta-oestradiol (20 μl aliquots from 0.008 nM to 100 nM, prepared from 10 mg in 10 ml ethanol) and test compounds, in concentrations of 1, 10, 100, 1000 μM, were pipetted into 96-well plates in a sterile flow hood. The solvent was left to evaporate for about 40 min.

The growth medium containing yeast was dispensed to all wells, except blank wells, in aliquots of 100 μl. The plates were incubated at 32° C. in a humidified atmosphere for 3 days, and then read at 540/360 nm by a microtiter plate reader (labsystems Muliskan Ascent Reader, Thermo labsystems, Vantaa, Finland).

Figure 11:
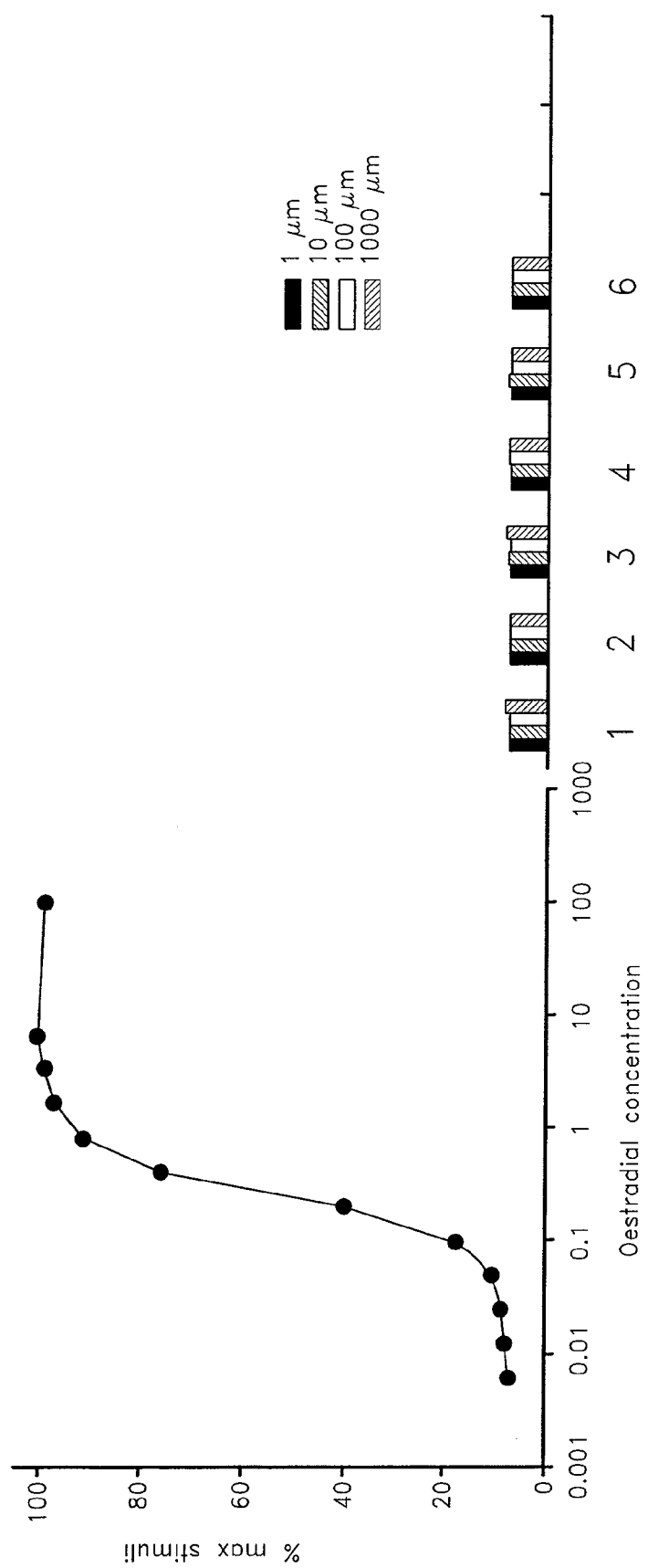
FIG. 11 illustrates that simmondsin compounds according to the invention have no significant oestrogen-like activity.

Results of the experiment are represented on FIG. 11. Tested compounds comprised (1) Z simmondsin-2'-ferulate; (2) E simmondsin-2'-ferulate, (3) 4-desmethylsimmondsin, (4) 5-desmethylsimmondsin, (5) 4,5-dimethylsimmdonsin and (6) didesmethylsimmondsin. Compared to the standards, it is clear that the tested compounds at the tested concentrations have no significant oestrogen-like activity.

The invention claimed is:

1. A method of inhibiting angiogenesis in humans and animals which comprises administering a therapeutically effective amount of a simmondsin, or esters or salts thereof, to the human or animal in need thereof wherein the simmondsin is selected from the group consisting of 4-desmethylsimmondsin, 5-desmethylsimmondsin, 4,5-didesmethylsimmondsin, 4,5-dimethylsimmondsin, 4-desmethylsimmondsin-2'-ferulate, 5-desmethylsimmondsin-2'-ferulate, 4,5-didesmethylsimmondsin-2'-ferulate, 4,5-dimethylsimmondsin-2'-ferulate, and any mixture thereof.

2. The method according to claim 1, whereby said simmondsin naturally occurs in jojoba and is comprised within jojoba flour or a jojoba extract.

3. The method according to claim 1, whereby said simmondsin is 4-desmethylsimmondsin.

4. The method according to claim 1 wherein said esters are ferulates.

5. The method according to claim 1, whereby said simmondsin is 5-desmethylsimmondsin.

6. The method according to claim 1, whereby said simmondsin is 4,5-didesmethylsimmondsin.

7. A method for inhibiting angiogenesis in humans and animals comprising administering a therapeutically effective amount of jojoba flour or an extract from jojoba flour to the human or animal in need thereof.

8. The method according to claim 1, whereby said simmondsin is 4,5-dimethylsimmondsin.

9. The method according to claim 1, whereby said simmondsin is 4-desmethylsimmondsin-2'-ferulate.

10. The method according to claim 1, whereby said simmondsin is 5-desmethylsimmondsin-2'-ferulate.

11. The method according to claim 1, whereby said simmondsin is 4,5-didesmethylsimmondsin-2'-ferulate.

12. The method according to claim 1, whereby said simmondsin is 4,5-dimethylsimmondsin-2'-ferulate.

* * * * *

UNITED STATES PATENT AND TRADEMARK OFFICE
CERTIFICATE OF CORRECTION

PATENT NO. : 7,387,999 B2
APPLICATION NO. : 10/520580
DATED : June 17, 2008
INVENTOR(S) : D'Oosterlynck et al.

It is certified that error appears in the above-identified patent and that said Letters Patent is hereby corrected as shown below:

First Page, Column 2, Abstract, Line 2, "a effective amount" should be changed to --an effective amount--

First Page, Column 2, Abstract, Line 16, "animals are disclosed" should be changed to --animals are disclosed.--

Drawings, Sheet 1 of 16, Line 2, "Ret=ott" should be changed to --Ret=off--

Drawings, Sheet 6 of 16, Y Axis Title, "H-Thymidine Incorporation (DPM)" should be changed to --$^3$H-Thymidine Incorporation (DPM)--

Drawings, Sheet 6 of 16, X Axis, Line 2, "5% 5%" should be changed to --% 5%--

Drawings, Sheet 9 of 16, Line 1, "15% confluency, contineous" should be changed to --15% confluency, continuous--

Drawings Sheet 11 of 16, Line 1, "100% confluency, contineous" should be changed to --100% confluency, continuous--

Column 5, Line 17, "(i. e. minimum" should be changed to --(i.e. minimum--

Column 5, Line 51, "an/or chemi-" should be changed to --and/or chemi- --

Columns 13-14, Line 31 (after structure), "—$CO_3H_7$" should be changed to -- —$OC_3H_7$--

Columns 15-16, Line 4 (after structure), "fewlate" should be changed to --ferulate--

Columns 17-18, Line 28 (after structure), "—OOOH" should be changed to -- —COOH--

Column 21, Line 1, "age-related maculopahty" should be changed to --age-related maculopathy--

Column 21, Line 66, "393402)." should be changed to --393-402).--

Column 25, Line 44, "or animal In need" should be changed to --or animal in need--

Column 27, Line 62, "etters 10:1439-1442)." should be changed to --Letters 10:1439-1442).--

UNITED STATES PATENT AND TRADEMARK OFFICE
CERTIFICATE OF CORRECTION

PATENT NO. : 7,387,999 B2
APPLICATION NO. : 10/520580
DATED : June 17, 2008
INVENTOR(S) : D'Oosterlynck et al.

It is certified that error appears in the above-identified patent and that said Letters Patent is hereby corrected as shown below:

Column 29, Line 45, "substantially pure)" should be changed to --substantially pure).--

Column 30, Line 2, "Res. 47 (1) 3140." should be changed to --Res. 47 (1) 31-40.--

Column 32, Line 33, "Al, A4, A5, B3 B4, B5, B6" should be changed to
--Al, A4, A5, B3, B4, B5, B6--

Column 32, Line 48, "by Cell Counting." should be changed to --by Cell Counting--

Column 35, Line 11, "simmondsin" should be changed to --simmondsin.--

Column 35, Line 30, "8 mg panthotenic acid," should be changed to --8 mg pantothenic acid,--

Column 36, Line 2, "540/360 nm by" should be changed to --540/360 nM by--

Signed and Sealed this

Sixth Day of October, 2009

David J. Kappos
*Director of the United States Patent and Trademark Office*

UNITED STATES PATENT AND TRADEMARK OFFICE
CERTIFICATE OF CORRECTION

PATENT NO.         : 7,387,999 B2                                       Page 1 of 1
APPLICATION NO. : 10/520580
DATED              : June 17, 2008
INVENTOR(S)        : D'Oosterlynck et al.

It is certified that error appears in the above-identified patent and that said Letters Patent is hereby corrected as shown below:

Column 10, Line 27, "$R_3. R_2', R_3' R_4'$," should be changed to -- $R_3, R_2', R_3', R_4'$,--

Column 11, Line 13, "wherein $R_3R_3' R_4'$," should be changed to --wherein $R_3, R_3', R_4'$,--

Signed and Sealed this

Tenth Day of November, 2009

David J. Kappos
*Director of the United States Patent and Trademark Office*